(12) United States Patent
Chauhan et al.

(10) Patent No.: US 12,186,425 B2
(45) Date of Patent: Jan. 7, 2025

(54) DEVICES AND METHODS FOR REDUCING CYSTINE CRYSTALS IN VIVO

(71) Applicant: University of Florida Research Foundation, Inc., Gainesville, FL (US)

(72) Inventors: Anuj Chauhan, Gainesville, FL (US); Phillip J. Dixon, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 41 days.

(21) Appl. No.: 17/455,359

(22) Filed: Nov. 17, 2021

(65) Prior Publication Data
US 2022/0079877 A1  Mar. 17, 2022

Related U.S. Application Data

(62) Division of application No. 16/649,541, filed as application No. PCT/US2018/052194 on Sep. 21, 2018, now abandoned.

(60) Provisional application No. 62/561,788, filed on Sep. 22, 2017.

(51) Int. Cl.
| | |
|---|---|
| *A61K 9/00* | (2006.01) |
| *A61K 9/14* | (2006.01) |
| *A61K 33/242* | (2019.01) |
| *A61K 47/32* | (2006.01) |
| *B29D 11/00* | (2006.01) |

(52) U.S. Cl.
CPC ............ *A61K 9/0051* (2013.01); *A61K 9/143* (2013.01); *A61K 33/242* (2019.01); *A61K 47/32* (2013.01); *B29D 11/00096* (2013.01)

(58) Field of Classification Search
CPC .... A61K 9/0051; A61K 33/242; A61K 9/143; A61K 47/32; B29D 11/00096
See application file for complete search history.

(56) References Cited

U.S. PATENT DOCUMENTS

| | | | |
|---|---|---|---|
| 6,528,601 | B1 | 3/2003 | Hara et al. |
| 7,438,411 | B2 | 10/2008 | Payne et al. |
| 2002/0197299 | A1 | 12/2002 | Vanderlaan et al. |
| 2008/0203592 | A1 | 8/2008 | Qiu et al. |
| 2008/0218686 | A1 | 9/2008 | Sharma et al. |
| 2010/0239637 | A1 | 9/2010 | Ciolino et al. |
| 2013/0011460 | A1 | 1/2013 | Liu et al. |
| 2013/0118127 | A1 | 5/2013 | Kolluru et al. |
| 2013/0235335 | A1 | 9/2013 | Forrest et al. |

(Continued)

FOREIGN PATENT DOCUMENTS

| | | | | |
|---|---|---|---|---|
| CN | 102770407 A | * | 11/2012 | ......... A61K 41/0019 |
| CN | 109124826 A | * | 1/2019 | |

OTHER PUBLICATIONS

Machine translation of CN-109124826-A via google translate, 2019 (Year: 2019).*

(Continued)

*Primary Examiner* — Bethany P Barham
*Assistant Examiner* — Ayaan A Alam
(74) *Attorney, Agent, or Firm* — Thomas| Horstemeyer, LLP

(57) ABSTRACT

According to some aspects, this application provides devices and methods for treating cystinosis in a patient. Removable intra-ocular devices and contact lenses containing cystine-sequestering materials effective for uptake of cystine from the eyes of a patient having cystinosis are provided. Methods of making the cystine-sequestering contact lenses are also provided.

11 Claims, 9 Drawing Sheets

(56) References Cited

U.S. PATENT DOCUMENTS

| | | | |
|---|---|---|---|
| 2015/0190278 A1 | 7/2015 | Gooding et al. | |
| 2015/0190279 A1 | 7/2015 | Acharya et al. | |
| 2016/0331705 A1 | 11/2016 | Dohil et al. | |
| 2016/0346224 A1* | 12/2016 | Macdonald | A61K 9/0051 |

OTHER PUBLICATIONS

Machine translation of CN-102770407-A from FIT via PE2E, 2012 (Year: 2012).*
Helaly, F. M., et al., Synthesis and characterization of nanosilver-silicone hydrogel composites for inhibition of bacteria growth, 2017, Contact Lens and Anterior Eye, 40, 59-66 (Year: 2017).*
Chen, K. et al., Preparation of Thermosensitive gold nanoparticles by plasma pretreatment and UV grafted polymerization, 2010, Thin Solid Films, 518, 7557-7562 (Year: 2010).*
International Search Report for PCT/US2018/052194 of Jan. 29, 2019.
Apyari et al., "Determination of cysteamine using label-free gold nanoparticles," Analytical Methods, 2012, vol. 4:10 pp. 3193-3199.
European Search Report dated May 11, 2021 in co-pending European Patent Application No. 18857596.3.
Shams, Fatemeh et al., "Treatment of corneal cystine crystal accumulation in patients with cystinosis", Clinical Ophthalmology, vol. 8, Jan. 1, 2014, pp. 2077-2084; https://www.dovepress.com/front_end/cr_data/cache/pdf/download_1619683817_608a69e9d8a6f/OPTH-36626-treatment-of-corneal-cystine-crystal-accumulation-in-patient_101014.pdf.
"Contact lenses with gold nanoparticles 'sandwiched' between the contact lens and a Tetrafilcon A layer," Gold Contact Lenses; Shekhar Eye Research India; http://shekhareye.com/gold-contact-lenses.html.

* cited by examiner

DEVICES AND METHODS FOR REDUCING CYSTINE CRYSTALS IN VIVO

CROSS-REFERENCE TO RELATED APPLICATIONS

This application is a divisional application of U.S. non-provisional application Ser. No. 16/649,541 filed on Mar. 20, 2020, which is the 35 U.S.C. § 371 national stage application of PCT Application No. PCT/US2018/052194, filed Sep. 21, 2018, where the PCT claims priority to, and the benefit of, U.S. provisional application entitled "Devices and Methods for Reducing cystine Crystals In Vivo" having Ser. No. 62/561,788, filed Sep. 22, 2017, each of which is herein incorporated by reference in its entirety.

BACKGROUND

Cystinosis is a metabolic disease characterized by the intracellular accumulation of cystine, the disulfide of the amino acid cysteine. In various organs, catabolism of proteins in the lysosomes of cells produces amino acids, which are then transported out of the cells to facilitate production of proteins. The amino acid cysteine forms the disulfide form, cystine, inside the lysosome, which exits the lysosome through cystinosin, a 367 amino acid integral membrane protein. Cystinosis is caused by mutations in the gene that encodes cystinosin. This defect leads to loss of the cystine efflux and subsequent accumulation above the solubility limit of 0.1 mg/mL, leading to crystal formation in the lysosome and eventual cell death.

Cystinosis patients appear normal at birth, but exhibit growth retardation, renal complications and hypothyroidism. Cystine crystals accumulate in various tissues including cornea and other ocular tissues such as the iris, conjunctiva, and retinal pigment epithelium (FIG. 1). A human cornea is a 500-550 μm thick, five layer structure including the corneal epithelium that contacts the tears, followed by the Bowman's layer, the corneal stroma (~400 μm thick), Descemet's membrane, and the corneal endothelium, which is in contact with the aqueous humor. The cystine accumulation is most severe in stroma, which is the thickest layer of the cornea. Typical cystinosis patients begin showing ocular symptoms at the age of 16 months, and, without appropriate treatment, the entire peripheral stroma and endothelium can become packed with crystals. By the age of 10 years, patients develop significant photophobia and, eventually, complications such as corneal scars can occur, resulting in irreversible damage to the eye. Current therapy for cystinosis involves treatment with cysteamine (β-mercaptoethylamine), which reacts with intralysosomal cystine to produce cysteine-cysteamine dimers and the amino acid cysteine, which can then be transported out of the lysosome via the lysine transport system and in the stroma of the eye can diffuse into tears and aqueous humor and be eliminated via drainage of these fluids from the eye naturally. However, cysteamine treatment presents some serious drawbacks, particularly for ocular treatment, including dosing limits required due to toxicity as well as issues with patient compliance with dosing schedule and the sometimes extended length of time required to obtain effective results.

BRIEF DESCRIPTION OF THE DRAWINGS

Further aspects of the present disclosure will be more readily appreciated upon review of the detailed description of its various embodiments, described below, when taken in conjunction with the accompanying drawings.

SUMMARY

Figure 1:
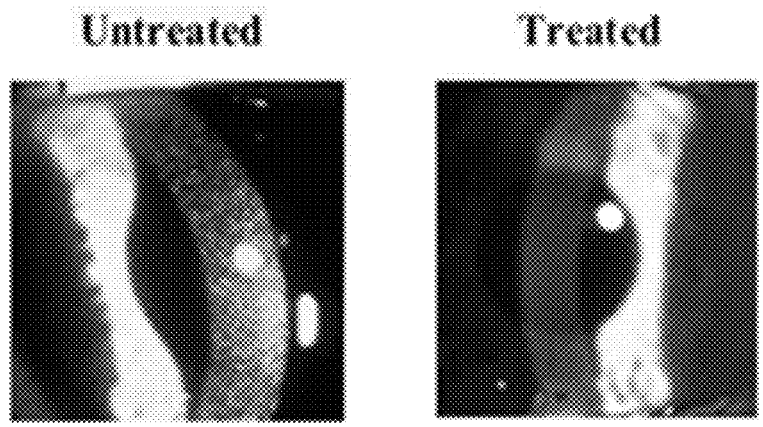
FIG. 1 is a slit lamp image illustrating an untreated and treated cornea in a cystinosis pediatric patient (from: William, Gahl, CRN conference, San Antonio, TX, 2007).

Briefly described, the present disclosure provides removable intra-ocular devices including a cystine-sequestering material effective to uptake about 30 µg or more of cystine/day from the eye of a patient having cystinosis.

The present disclosure also provides, in embodiments, contact lenses including: a contact lens base material selected from hydrogel or silicon hydrogel, and nanoparticles including a cystine-sequestering material. In such embodiments, the nanoparticles are incorporated into the contact lens with the base material, coated on a surface of the contact lens, or both, such that the cystine-sequestering material is present in an amount effective to uptake about 30 µg or more of cystine/day.

The present disclosure also provides methods of making disposable, cystine-sequestering contact lenses of the present disclosure. In embodiments, such methods include: providing a pre-formed contact lens having a contact lens matrix or providing a contact lens base material precursor capable of forming a contact lens matrix; providing a cystine-sequestering material selected from: gold nanoparticles, metallic nanoparticles capable of binding cystine, methacrylic acids, hydroxyethyl methacrylate, thiolated compounds, monomers of these compounds, combinations thereof, and precursors thereof; combining the pre-formed contact lens or the contact lens base material with the cystine-sequestering material or precursors; and forming the disposable cystine-sequestering contact lens having the cystine-sequestering material within the contact lens matrix in an amount effective to uptake cystine from the eye of a patient.

Methods of using the devices and contact lenses of the present disclosure are also provided. Methods of treating cystinosis, according to some embodiments of the present disclosure, include: providing, for a patient in need of treatment for cystinosis, a disposable contact lens of any of aspects 11-25 with instructions to wear the contact lens in the eye of the patient for at least 8 hours/day, where the contact lens is effective to remove about 70 µg, or more, of cystine per day from the eye of the patient.

Other systems, methods, features, and advantages of the present disclosure will be or will become apparent to one with skill in the art upon examination of the following drawings and detailed description. It is intended that all such additional systems, methods, features, and advantages be included within this description, and be within the scope of the present disclosure.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biochemistry, biology, molecular biology, material science and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

All publications and patents cited in this specification are cited to disclose and describe the methods and/or materials in connection with which the publications are cited. Publications and patents that are incorporated by reference, where noted, are incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. Any terms not specifically defined within the instant application, including terms of art, are interpreted as would be understood by one of ordinary skill in the relevant art; thus, is not intended for any such terms to be defined by a lexicographical definition in any cited art, whether or not incorporated by reference herein, including but not limited to, published patents and patent applications. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

It must be noted that, as used in the specification and the appended claims, the singular forms "a," "an," and "the" include plural referents unless the context clearly dictates otherwise. Thus, for example, reference to "a cell" includes a plurality of cells. In this specification and in the claims that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

As used herein the term "sequester" or "sequestered" indicates that a material (e.g., a compound) is taken up from one environment (e.g., an aqueous humor or cornea of an eye) and then bound or otherwise immobilized to a second material such that it can be removed from the environment.

As used herein, "cystine-sequestering material" refers to materials described herein that are adapted to/configured to/capable of cystine uptake (e.g., by binding to, reacting with, coupling, or otherwise sequestering) cystine, such that the cystine can be removed from an undesired location (e.g., the aqueous humor, tears, cornea, or other ocular area, or bloodstream and tissues of a patient). Materials capable of uptake of cystine may have the natural ability to bind, react with, couple, or otherwise sequester cystine and may also be further engineered/modified (e.g., configured to/adapted to) to optimize the cystine uptake (e.g., the amount, time, capacity, etc.) by the material. In embodiments, cystine-sequestering materials of the present disclosure have been configured/engineered/adapted to be "effective to" sequester/uptake certain amounts of cystine over specified time in order to treat a subject suffering from Cystinosis.

The term "host," "subject," or "patient" refers to any living entity in need of treatment, including humans, mammals (e.g., cats, dogs, horses, mice, rats, pigs, hogs, cows, and other cattle), birds (e.g., chickens), and other living species that are in need of treatment. In particular, the terms "host"/"subject"/"patient" include humans. As used herein, the term "human host" or "human subject/patient" is generally used to refer to human hosts. In the present disclosure the term "host" typically refers to a human host, so when used alone in the present disclosure, the word "host" refers to a human host unless the context clearly indicates the intent to indicate a non-human host. Hosts that are "predisposed to" condition(s) can be defined as hosts that do not exhibit overt symptoms of one or more of these conditions but that are genetically, physiologically, or otherwise at risk of developing one or more of these conditions.

The terms "treat", "treating", and "treatment" are an approach for obtaining beneficial or desired clinical results. Specifically, beneficial or desired clinical results include, but are not limited to, alleviation of symptoms, diminishment of extent of disease, stabilization (e.g., not worsening) of disease, delaying or slowing of disease progression, substantially preventing spread of disease, amelioration or palliation of the disease state, and remission (partial or total) whether detectable or undetectable. In addition, "treat", "treating", and "treatment" can also be therapeutic in terms of a partial or complete cure for a disease and/or adverse effect attributable to the disease.

As used herein, the terms "prevent," "prophylactically treat," or "prophylactically treating" refer to completely, substantially, or partially preventing a disease/condition or one or more symptoms thereof in a host/patient. Similarly, "delaying the onset of a condition" can also be included in "prophylactically treating", and refers to the act of increasing the time before the actual onset of a condition in a patient that is predisposed to the condition.

As used herein, the term "biocompatible" refers to the ability to co-exist with a living biological substance and/or biological system (e.g., a cell, cellular components, living tissue, organ, etc.) without exerting undue stress, toxicity, or adverse effects on the biological substance or system.

As used herein, the term "contact lens base material" refers to materials used to form a contact lens, such as hydrogels, silicon, methacrylic acid, hydroxyethyl methacrylate (HEMA), and the like, described below. Similarly, the term "contact lens matrix material" also refers to materials that form a contact lens, but when those materials have been polymerized to form a matrix that gives structure to the lens. For instance, while silicon and/or methacrylic acid may be the base materials in a contact lens, upon polymerization and forming of the lens, these materials crosslink to form a contact lens matrix. Thus, "contact lens base materials" may refer to precursor materials (e.g., prior to polymerization) but may also just refer to the materials present in the matrix, whereas the matrix refers to the compound and the structure.

Discussion

In accordance with the purpose(s) of the present disclosure, as embodied and broadly described herein, embodiments of the present disclosure, in some aspects, relate to methods of treating cystinosis in a patient as well as devices, including contact lenses, other ocular devices, skin patches, and other removable medical devices capable of sequestering cystine from a patient and thereby reducing formation and accumulation of cystine crystals in vivo in a patient. The present disclosure also includes methods of making the lenses and devices of the present disclosure and of using them for the treatment of cystinosis.

Figure 2:
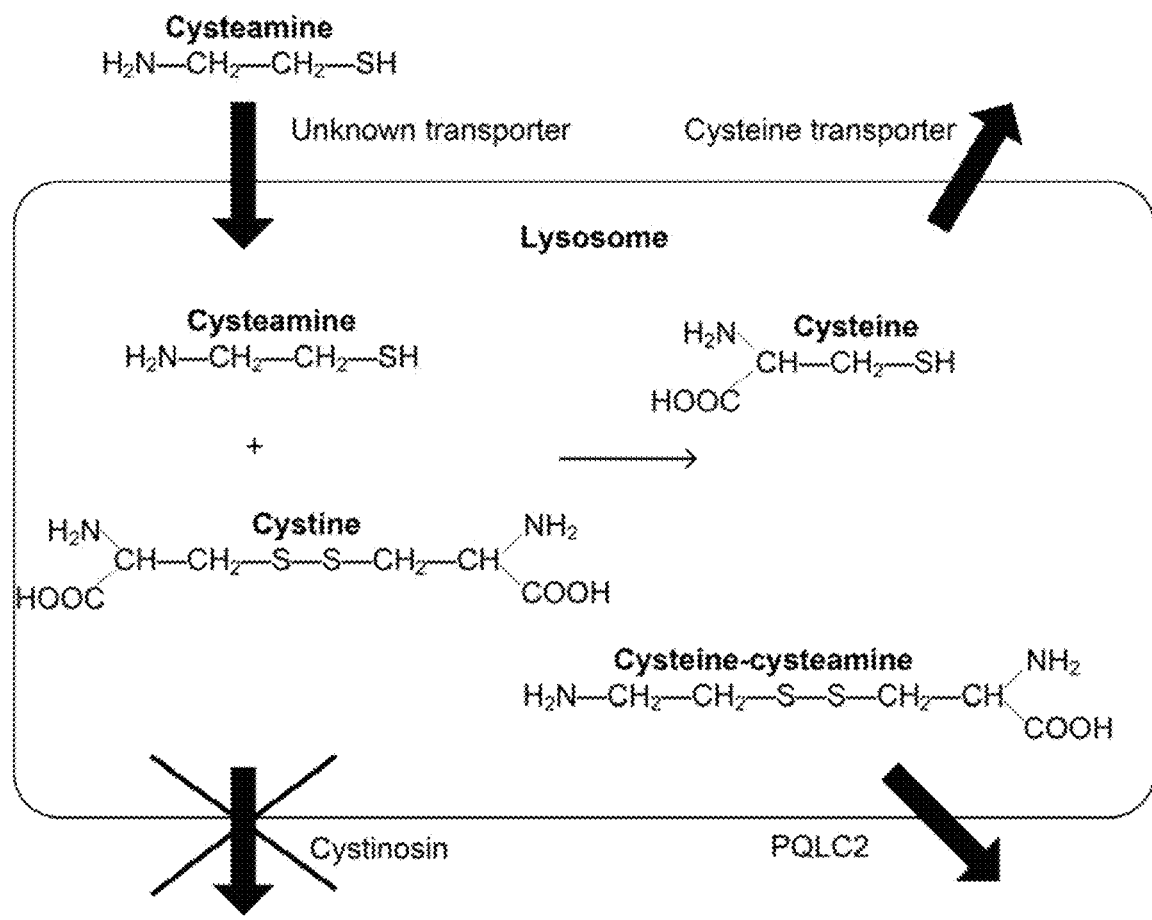
FIG. 2 illustrates a mechanism of lysosomal cystine depletion by cysteamine. Cysteamine enters the lysosome through an unknown transporter and reacts with cystine. This results in formation of cysteine and a new cysteine-cysteamine mixed disulfide, each of which can exit the lysosome through its own transporter. (from: Improving the prognosis of nephropathic cystinosis, Besouw M T P, Levtchenko E N, Dove Press, 17 Jul. 2014 Volume 2014:7 Pages 297-302).
Figure 3:
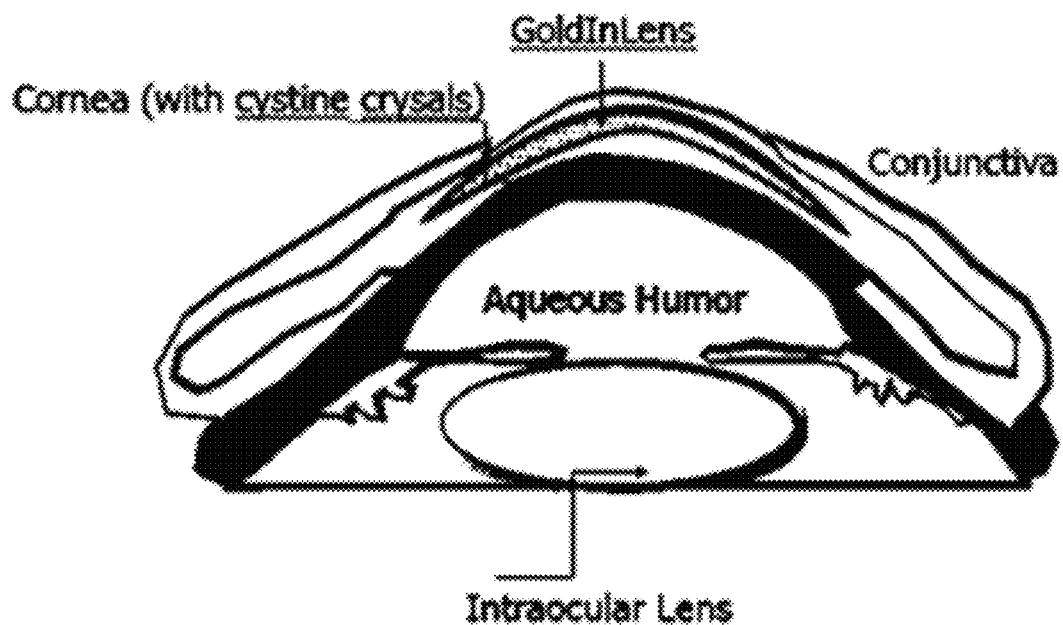
FIG. 3 is a schematic illustration of an embodiment of a contact lens of the present disclosure (e.g., GoldInLens™). The dimensions of each layer and the sequence of steps are described in FIG. 4.

Cystinosis is commonly treated with cysteamine (β-mercaptoethylamine), which reacts with intralysosomal cystine to produce mixed disulfide cysteine-cysteamine dimers (FIG. 2) and the amino acid cysteine. These are transported out of the lysosome via the lysine transport system, bypassing the damaged cystinosis transporter. In the eyes though, a significant portion of the cystine is extra-cellular, and much of it is dispersed in the water-like stoma layer of the cornea. The polymer in the stroma can also play a role in crystallization of the cystine in the stroma. The products from the cysteamine-cystine reaction can diffuse from the stroma both into the tears and the aqueous humor, where these are cleared through tear and aqueous humor drainage, respectively (see FIG. 3 for the anatomy).

The oral dose of cysteamine given to treat cystinosis systemically achieves therapeutic effects in several organs, but its concentration in corneal tissue is inadequate to reduce crystal accumulation. Thus, cysteamine eye drops, delivered hourly, are utilized for treating the ocular complications of cystinosis. The drug cysteamine diffuses into the cornea to react with cysteine, which leads to formation of products that are water soluble and can be cleared from the eye mainly by drainage of the aqueous humor. The solubility limit of cystine is about 0.1 mg/mL, while the total concentration of cystine crystals in the cornea can be as high as 1-10%. In current protocol of delivery of cysteamine through hourly instillation of 0.55% (50 mM) eye drops, the concentration of drugs in the eye drops is limited to 0.55% because higher concentrations caused toxicity in rabbits.

The known bioavailability of other drugs typically ranges from 1-5% for delivery by eye drops. Thus, each 0.55% 25 μl cysteamine drop would be expected to deliver a maximum of 6.5 μg to the cornea. With an hourly eye drop instillation over 8 hours, a maximum of 50 μg of drug will reach the corneal tissue each day, leading to dissolution of about 100 μg of cystine. The total mass of cystine in a stroma of a diseased patient is difficult to quantify, but it could be a few milligrams. For 10 mg of crystals, it takes about 200 days to clear the crystals. Furthermore, deposition of cystine continues to occur during this period, so the actual time needed for clearance of the crystals after treatment begins is a few years. The length of time required for clearance of crystals could be reduced if higher drug concentrations could be used in eye drops or if more eye drops could be delivered each day. Neither of these is a viable option because toxicity prevents use of higher concentration, while patient compliance with a regimen of more than 8 drops each day will likely be very poor.

The eye-drop based therapy suffers from other potential problems related to drug stability and compliance. The cysteamine eye drop formulation (Cystaran™) is required to be kept frozen at temperatures <−15° C., and after thawing it has a maximum shelf life of a week, even under refrigerated conditions, due to oxidation into an inactive form. A more severe problem with the eye drop based cysteamine therapy is the potential for poor compliance, a problem intrinsic to chronic ocular diseases treated with eye drops. Cysteamine eye drops are not effective at three or four times daily dosing regimens and must be administered six-twelve times a day to every hour while awake. This high frequency of drop instillation often leads to poor compliance, and thus limitation of the therapeutic benefits and disease progression.

The above-described drawbacks related to the use of cysteamine eye drops for treatment of ocular symptoms of cystinosis, as discussed above, have driven the need for alternative methods to treat cystinosis. The present disclosure provides drug free devices and methods for treating the condition.

In one approach, contact lenses were developed to be used for cysteamine therapy due to the high corneal bioavailability (estimated to be as large as 50%). On insertion of a contact lens, the tear film partitions into a pre (PLTF) and post (POLTF) contact lens tear films, which both are a few microns in thickness (see FIG. 3 for the anatomy). Since POLTF is very thin (~5 μm), almost the entire drug amount released into the POLTF by the contact lens diffuses into the cornea, which is the target tissue for cystinosis. However, commercial lenses cannot be used for sustained release of small molecules like cysteamine because a majority of the loaded drug is released in a short time period.

To prolong drug release durations, vitamin E-loaded contact lenses were developed as described generally in U.S. Pat. No. 8,404,265 (which is hereby incorporated by reference herein), which increased the release duration because vitamin E acts as a diffusion barrier. Contact lens-based cysteamine delivery also eliminates the disadvantages of the preservatives in the multi-use eye drop formulations, which can cause significant toxicity due to the very high frequency of eye drops instilled by the patients. While cysteamine-loaded contact lens will likely improve compliance over the drop protocol, there is a potential for toxicity from continuous exposure of the cornea to the drug, which is a strongly oxidizing molecule. Another challenge is retaining the efficacy of the drug-loaded lens during the long shelf life before use, which is difficult because the drug is very prone to oxidation. Even during the contact lens wear, a portion of the drug will be oxidized, reducing the efficacy of the system. The methods, lenses, and devices of the present disclosure utilize the contact lens platform, allowing improved access to the cornea, but eliminate the potential toxicity and other drawbacks associated with using a contact lens for drug delivery.

It is not believed that contact lenses with the ability to react with, sequester, or otherwise remove cystine have been provided or used for the treatment of cystinosis or otherwise. Approaches for integrating or depositing nanoparticles within/onto contact lenses have been applied to other purposes, such as altering the optical density and spectral transmission or reflectance of contact lenses, as described in US 20130235335 A1. This approach involved gold nanoparticle solutions with a relatively low concentration and large diameter gold particles, which would provide ineffective cystine binding.

In another approach, a protective contact lens was provided with nanoparticles embedded or coated on the lens to extinguish near-infrared energy, as described in U.S. Pat. No. 7,438,411 B2. The approach describes use of tunable nanoshells having a dielectric core and a metal shell. With the capability to alter the relative size of the core and the metal shell, nanoshells are tunable, allowing a range of optical extinctions. Due to the low ratio of metal in the nanshoells, the gold loading in the lens would be insufficient and ineffective, and any cysteine uptake would be negligible.

Figure 4:
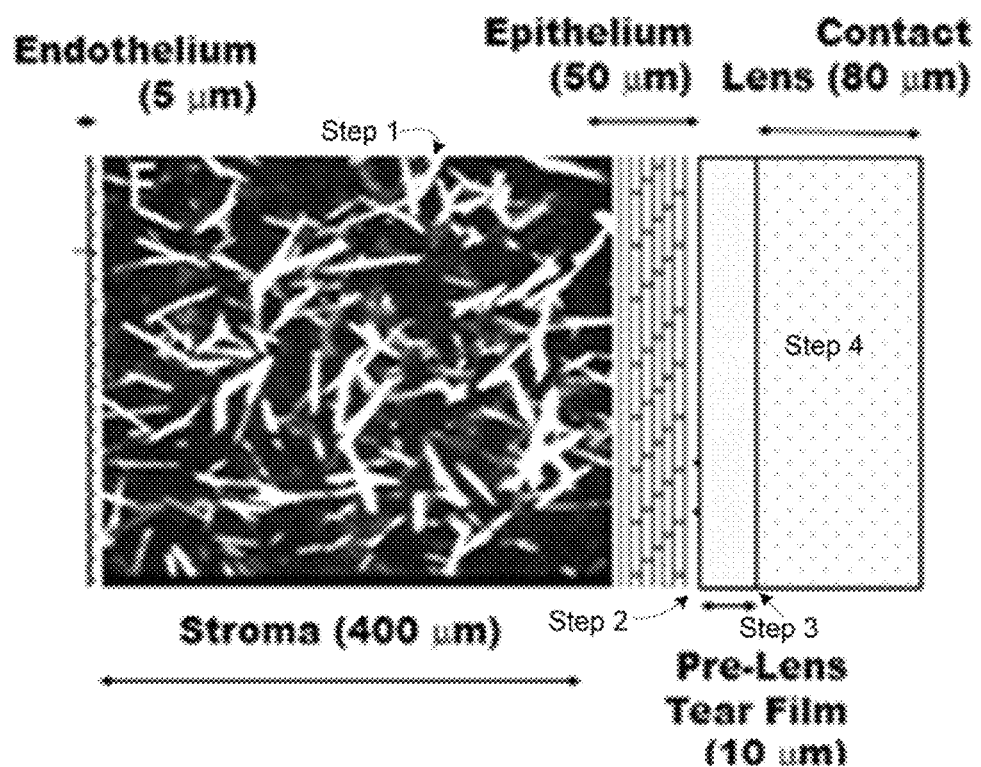
FIG. 4 illustrates details of the sequence of steps involved in an embodiment of transport and reaction of cystine for treatment of cystinosis by a contact lens of the present disclosure. Step 1: cysteine crystals in stroma dissolve to keep concentration of dissolved cysteine at solubility limit of 0.1 mg/mL. Step 2: Molecular cysteine diffuses across stroma and epithelium to reach tears. Step 3: Cystine diffuses into contact lens. Step 4: Cystine reacts/binds to cysteine-sequestering material in the lens.

The present disclosure provides new methods, ocular devices, and lenses for treating ocular cystinosis without the need for cysteamine or other drug. Instead of dissolving crystals due to reaction of cystine with cysteamine in the cornea, the methods and devices of the present disclosure provide an intra-ocular device, such as a contact lens, designed such that it has a capacity for reacting with or otherwise sequestering cystine to remove the cystine from the eye of the wearer. As cystine in the tears diffuses into the lenses to react with the nanomaterials, cystine will diffuse from the eyes towards the tears and contact lens, thereby causing dissolution of the crystals. This is illustrated generally in FIGS. 3 and 4. The lens, containing the sequestered cystine can then be discarded, and a new one used each day, or as needed.

The present disclosure provides multiple approaches for sequestering cystine in intra-ocular devices, such as contact lenses. In embodiments, a contact lens of the present disclosure includes at least one cystine-sequestering material. In embodiments, the cystine-sequestering material includes a particle or compound either incorporated/embedded in a contact lens material and/or coated on the surface of the lens that has the ability to and is effective to react with (e.g., chemically change or bind with) cystine and thereby take up (sequester) the cystine in/on the lens, such that when the lens is removed and discarded, the cystine is also removed. As described in greater detail below, in embodiments, the cystine-sequestering material comprises metallic nanoparticles (e.g., gold nanoparticles), polymeric nanoparticles made from monomers with a high affinity for cystine (e.g., methacrylic acid, a combination of methacrylic acid and hydroxyethyl methacrylate, thiolated compounds (e.g., thiolated acrylates), monomers of these materials, and combinations thereof.

An aspect of the present disclosure includes contact lenses including, as the cystine sequestering material, nanoparticles (e.g., incorporated within the contact lens or coated on a surface of the contact lens) that have a high capacity for binding cystine. Multiple mechanisms can used in the design of such nanoparticles. For example, the nanoparticles can be metallic nanoparticles capable of binding and retaining cytine such that cystine reacts with the surface of the metallic particles to bind irreversibly, thereby removing the bound cystine with the lens. In an embodiment, the metallic nanoparticles are gold particles. The presence of gold particles can make the lens colored due to the plasmon resonance effect.

The examples below describe lenses of various materials including gold particles that are capable of binding cystine and methods of making the lenses. As described in greater detail below, in embodiments, the lenses include the nanoparticles embedded in the lens material, and in other embodiments, pre-made lenses can be coated/functionalized with the metal (e.g., gold) nanoparticles.

For lenses made with particles embedded in the lens, in embodiments the particles are pre-formed and mixed with the monomers used to make the lens prior to polymerization, such that the metallic particles are embedded in the formed lens. In other embodiments, precursor materials for the metallic nanoparticles can be combined with the lens materials, and then the nanoparticles can be formed in situ during lens formation.

In embodiments, the particles can be polymeric particles that are imprinted to achieve high partitioning. Alternatively, particles can be polymeric particles made of monomers with a high affinity for cystine, such as, but not limited to, methacrylic acid. Alternatively, contact lens can be prepared by using monomers that have a high affinity for cystine. The examples below demonstrate that that gels with 75% methacrylic acid and 25% hydroxyethyl methacrylate bind substantial amounts of cystine. The particles could also include monomers that react with cystine, such as, but not limited to, thiolated compounds (such as, but not limited to, thiolated acrylates) that react with cystine through the thiol group. In some embodiments, including thiols into the contact lens can lead to reaction of cystine in a similar manner as the drug cysteamine reacts with cystine. In embodiments, thiolated acrylates could be used as monomers to make the lens or, alternatively, thiolated polymers could be included into the lens after polymerization.

Lenses of the present disclosure can also include a combination of such cysteine sequestering approaches (e.g., gold particles and/or methacrylic acid particles, and/or thiolated acrylates or other combinations.) In such embodiments, the size of the nanoparticles could be from a few nm to about 200 nm to ensure minimal impact on transparency. In embodiments, the volume loaded would be such that a 30 mg lens loaded with the particles is effective to sequester about 20 micrograms or more of cystine/day. In embodiments, the particles in the lens can sequester 10 micrograms or more. In other embodiment, the particles can sequester 20 micrograms or more, and in yet other embodiments, they can sequester 100 micrograms or more of cystine.

In embodiments, contact lenses of the present disclosure include a monomer that has a high affinity for cystine. For example, the examples below demonstrate the discovery that hydrogels made up of 75% methacrylic acid and 25% hydroxyl ethyl methacrylate bind substantially more cystine compared to commercial contact lenses of comparable weight and size. Increasing the methacrylic acid fraction of such lenses will likely further increase the amount of cystine adsorbed. In embodiments, other polymers capable of binding cystine, such as, but not limited to, acrylic acid, can also be used. In embodiments, contact lenses can be loaded with either molecules or polymers that have a high affinity for cystine. In an embodiment, a polymer of methacrylic acid can be loaded into the contact lenses. Benzalkonium chloride is a cationic surfactant incorporation of which into the contact lenses can increase the affinity for cystine through interactions with the carboxylic group on cystine. Similarly, many other ionic surfactants or monomers or polymers can be used to interact with either the cationic amine group or the anionic carboxylic group on cystine.

Thus, as described briefly above and in greater detail in some of the examples below, embodiments of the present disclosure include removable intra-ocular devices (such as, but not limited to, contact lenses, fornix inserts, puncta plugs, corneal rings, scleral lenses, sub-conjunctiva inserts, and intra cameral inserts into the aqueous humor) that include a cystine-sequestering material effective to uptake about 30 μg or more (in some embodiments 70 μg or more, in some embodiments 70-200 μg or more) of cystine/day from the eye of a patient having cystinosis.

Embodiments of the present disclosure also include contact lenses made of at least a base material (e.g., hydrogel or silicon hydrogel) and nanoparticles including a cystine-sequestering material, where the nanoparticles are incorporated in or coated on the contact lens. In embodiments, the cystine-sequestering material is present in an amount effective for uptake of about 30 μg or more of cystine/day (in some embodiments about 70 μg or more, in some embodiments about 70-200 μg or more, in some embodiments about 200 μg or more (e.g., 1000 μg)). As discussed above, in embodiments, the cystine-sequestering material is selected from gold nanoparticles, other metallic nanoparticles capable of binding cystine, methacrylic acids, hydroxyethyl methacrylate, thiolated compounds, monomers of these compounds, and combinations of these. In some embodiments, the cystine-sequestering material is gold nanoparticles, and in some embodiments the gold nanoparticles have an average size of about 10 nm-30 nm. In some embodiments, the gold nanoparticles have an average size of about 1 nm-10 nm. In embodiments, the loading of gold nanoparticles in the contact lens is about 0.2%-10%; in some embodiments it is 5% or more. Although greater than about 10% gold in the lens may produce too much coloration in the lens for daytime wear, higher amounts could be used in lenses just worn for sleep. Thus, in embodiments contact lenses of the present disclosure can have from about 0.2% up to about 30% gold nanoparticles.

In some embodiments of the contact lenses of the present disclosure, the lens base material is selected from hydroxyethyl methacrylate (HEMA), methacrylic acid, silicone-hydrogel, and combinations thereof. In some embodiments, the base material is a combination of methacrylic acid and hydroxyethyl methacrylate. In embodiments, the base materials can be combined in various ratios. For example, in an embodiment, the base material comprises about 75% methacrylic acid and about 25% hydroxyethyl methacrylate, and in another example embodiment, the base material includes about 100% methacrylic acid with small fraction of cross-linker to ensure mechanical strength.

In some embodiments, the cystine-sequestering material includes a combination of gold nanoparticles and methacrylic acid. In some embodiments, the contact lens includes a combination of gold nanoparticles and thiolated acrylates. These and other combinations and embodiments of the above materials can be used to provide cystine-sequestering contact lenses of the present disclosure.

In some embodiments, in addition to sequestering cystine, the contact lens can also release the drug cysteamine to achieve a dual-mode therapy. This design can be particularly useful to patients that already have significant deposits of cystine crystals, where faster dissolution is needed and/or desired. After crystals have dissolved or significantly reduced in volume, the patient can switch to wearing a lens without the drug as a maintenance therapy so no further crystal aggregation occurs.

In the lens designed for the dual therapy approach, vitamin E can be incorporated into the lens to create a slow release of the drug. In embodiments, to load vitamin E, gold nanoparticles (or other cystine-sequestering material), and drug, it would be preferable to first load vitamin E by soaking the lens in a solution of vitamin E in ethanol, followed by extraction of ethanol. In embodiments, gold can then be loaded via the in situ approach, described in more detail below. Since vitamin E is insoluble in aqueous solutions, the vitamin E loaded in the lens will not diffuse out. In some embodiments, the drug cysteamine can then be loaded by soaking the gold and vitamin E loaded lens in the drug.

In additional embodiments, the contact lens can also potentially slowly release hydronium ions to decrease the pH in tears and thereby increase the solubility of cystine in tears as well as in the stroma. This will lead to faster elimination of cystine and also higher binding of cystine into the contact lens. To achieve this, the contact lens can contain an acid that ionizes at the physiological pH. Examples of acids that can be used for this purpose include, but are not limited to, citric acid, formic acid, ascorbic acid, benzoic acid, acetic acid, and any other biocompatible acid. The pH of the tears must be kept within the safe range, so, in embodiments, controlled release of the acid due to vitamin E barriers can be used.

Additionally, although the examples below focus on contact lenses of the present disclosure, the approaches described herein can be applied to other ophthalmic devices, such as but not limited to, fornix inserts, puncta plugs, corneal rings, scleral lenses, sub-conjunctiva inserts, intra cameral inserts into the aqueous humor, etc. In inserts that do not block vision, the particle size and loading can be considerably higher since transmission of visible light is not required. The devices of the present disclosure are made of biocompatible materials, since they are used in vivo in a patient. Such devices can also be designed to last a few months and so will have cystine capacity that is at least 20-30 times the cystine sequestration capacity of the contact lenses that are replaced daily. Also, it will be preferable if the devices that are injected or implanted are prepared from biodegradable materials such as PLGA, PCL, etc. For example, a 0.1 g gel containing 20% of 10 nm size gold particles will contain sufficient surface area to bind about 2-3 g of cystine. Further increasing the weight of the gel and/or reducing particle size and/or increasing particle loading can provide sufficient capacity to clear the crystals. Degradation of the device would then slowly release the cystine coated particles and cleared through the various flow pathways.

Furthermore, devices designed to sequester cystine are not necessarily limited to ophthalmic application. The present disclosure also envisions other removable devices that can be temporarily applied to a patient to sequester cystine from skin or directly from blood, such as, but not limited to, skin patches. Thus, in embodiments, the present disclosure also includes medical devices incorporating the materials described above that can be temporarily applied to the epidermis of a patient in order to draw cystine from the patient and sequester it in the device until removal. In an embodiment, the device is an epidermal patch including any of the cystine sequestering materials described above, where the patch can be applied to the skin of a patient and will cause cystine to diffuse from the body (e.g., blood, via capillaries, etc.), through the skin, to the patch, which can then be removed and discarded.

As described in conjunction with the description of the cystine sequestering contact lenses above, the present disclosure also includes methods of making these disposable, cystine-sequestering contact lenses. Such methods are described briefly above, and some embodiments are discussed in greater detail below. Briefly, the present disclosure includes methods of making disposable cystine-sequestering contact lenses of the present disclosure from pre-formed (e.g., commercially available) contact lenses or by preparing them from precursor materials.

In embodiments where the lenses of the present disclosure are made from a pre-formed contact lens, the lens can include commercially available hydroxyethyl methacrylate lens (HEMA) or a silicone-hydrogel lens, where the HEMA and/or silicone-hydrogel lens has a contact lens matrix (a 3-dimensional structure based on the crosslinking between the components of the lens). In embodiments, this matrix includes microscopic spaces/pores in which nanoparitcles of cystine-sequestering material can be embedded, such as by forming the nanoparticles in situ in the lens matrix.

In embodiments, the cystine-sequestering material can be selected from, but not necessarily limited to: gold nanoparticles, other metallic nanoparticles capable of binding cystine, methacrylic acids, hydroxyethyl methacrylate, thiolated compounds, monomers of these compounds, combinations thereof, and precursors thereof, such as described above. In some embodiments where the cystine-sequestering material includes gold nanoparticles, the particles can be formed in the pre-formed lens in situ by soaking the pre-formed lens in gold precursor materials. In embodiments, the lens is first soaked in gold chloride (e.g., chloroauric acid) followed by soaking the lens in a mixture of citric acid and gold chloride, such that nanoscale gold particles form within pores of the pre-formed lens matrix material. In embodiments, the chloroauric acid has a concentration of about 0.1-5%, and the citric acid has a concentration of about 2-15 times the concentration of the gold precursor. In embodiments, the ratio of citric acid to chloroauric acid is from about 1 to 15. In embodiments, the reduction of gold chloride to form the gold particles is achieved by other reducing molecules such as, but not limited to, oxalic acid, salicylic acid, water-soluble salts, such as alkali metals salts, of these acids; glucose, hydroquinone, including also substituted hydroquinones such as bromo and chlorohydroquinone and lower alkyl substituents such as methyl and dimethyl-hydroquinone; sodium and potassium sulfites, and mixtures of these loaded into the contact lens or integrated into the contact lens matrix.

In embodiments where a pre-formed contact lens is not used, the cystine-sequestering material can also be mixed with a contact lens base material precursor to incorporate the cystine-sequestering material into the lens upon formation. In embodiments, the contact lens base material precursor is a hydroxyethyl methacrylate lens (HEMA) monomer. In embodiments, the method of forming the contact lens of the present disclosure includes mixing the HEMA monomer with an aqueous phase comprising gold nanoparticles and a crosslinker, placing the mixture in a mold, and polymerizing the HEMA monomer such that the gold nanoparticles are embedded in a HEMA polymer matrix. In some such embodiments, the gold nanoparticles are pre-formed. In embodiments, the gold nanoparticles have a concentration ranging from 1-5%. In embodiments, the crosslinker is ethylene glycol dimethacrylate (EGDMA). In some embodiments, before polymerization of the lens base material precursors, additional monomers that also have some cystine-sequestering ability can be added to the mixture, (such as, but not limited to, thiolated methacrylates, tert butyl methacrylate (tBM), methacrylic acid (MAA), hydroxyethyl methacrylate (HEMA), and combinations thereof). In such embodiments, these additional cystine-sequestering materials can improve the cystine-sequestering function of the lenses.

The present disclosure also includes methods of treating cystinosis using the devices described above. In an embodiment, the present disclosure includes a method of treating cystinosis in a patient, by providing to a patient in need of treatment for cystinosis, a disposable contact lens of the present disclosure that includes a cystine sequestering material and providing instructions to wear the contact lens in the eye of the patient for at least 8 hours/day. Methods of treating cystinosis include applying to the eyes of the patient, a disposable contact lens of the present disclosure as described above. The lens is left in the eye(s) of the patient for at least 1 hour/day but preferably 4 hours or longer, and more preferably at least 8 hours/day. In embodiments, the contact lens is effective to remove about 70 µg, or more, of cystine per day from the eye(s) of the patient, after which it can be discarded. It will be understood that the lens may actually remove more or less than 70 µg depending on compliance with instructions, actual time worn, and the like. For patients needing vision correction, the contact lens can be designed with the required refractive power. For such cases, the patient can wear the lens even after the cystine uptake capacity is saturated. For example, the patient could wear the lens during the entire day. Lenses that are worn continuously for longer than a day can also be used for cystine sequestration but higher mass of cystine sequestration will be needed to ensure that the lens continues to remove cystine for a majority of the wear time. In embodiments, the lens of the present disclosure is capable of removing/holding from about 20-200 µg.

Additional details regarding the methods, compositions, and organisms of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

ASPECTS

The following listing of exemplary aspects supports and is supported by the disclosure provided herein.

Aspect 1. A removable intra-ocular device comprising:
a cystine-sequestering material effective to uptake about 30 µg or more of cystine/day from the eye of a patient having cystinosis.

Aspect 2. The removable intra-ocular device of aspect 1, wherein the intra-ocular device is selected from the group consisting of: a contact lens, fornix inserts, puncta plugs, corneal rings, scleral lenses, sub-conjunctiva inserts, and intra cameral inserts into the aqueous humor.

Aspect 3. The removable intra-ocular device of aspect 1 or 2, wherein the cystine-sequestering material is effective to uptake about 70-200 μg of cystine/day.

Aspect 4. The removable intra-ocular device of any of aspects 1-3, wherein the cystine-sequestering material is selected from gold nanoparticles, metallic nanoparticles capable of binding cystine, methacrylic acids, hydroxyethyl methacrylate, thiolated compounds, monomers of these compounds, and combinations thereof.

Aspect 5. The removable intra-ocular device of any of aspects 1-4, wherein the cystine-sequestering material comprises gold nanoparticles.

Aspect 6. The removable intra-ocular device of aspect 4 or 5, wherein the gold nanoparticles have an average size of about 10 nm-30 nm.

Aspect 7. The removable intra-ocular device of aspect 4 or 5, wherein the gold nanoparticles have an average size of about 10 nm or less.

Aspect 8. The removable intra-ocular device of any of aspects 4-7, wherein the loading of gold nanoparticles in the intra-ocular device is about 5% or more.

Aspect 9. The removable intra-ocular device of any of aspects 4-7, wherein the loading of gold nanoparticles in the intra-ocular device is about 0.2%-10%.

Aspect 10. The intra-ocular device of any of aspects 1-9, wherein the cystine-sequestering material comprises a combination of gold nanoparticles and methacrylic acid.

Aspect 11. A contact lens comprising:
a contact lens base material selected from hydrogel or silicon hydrogel, and
nanoparticles comprising a cystine-sequestering material, wherein the nanoparticles are incorporated into the contact lens with the base material, coated on a surface of the contact lens, or both, wherein the cystine-sequestering material is present in an amount effective to uptake about 30 μg or more of cystine/day.

Aspect 12. The contact lens of aspect 11, wherein the cystine-sequestering material is capable of uptake of about 70-200 μg of cystine/day.

Aspect 13. The contact lens of aspect 11, wherein the cystine-sequestering material is capable of uptake of about 200 μg or more of cystine/day.

Aspect 14. The contact lens of any of aspects 11-13, wherein the cystine-sequestering material is selected from gold nanoparticles, metallic nanoparticles capable of binding cystine, methacrylic acids, hydroxyethyl methacrylate, thiolated compounds, monomers of these compounds, and combinations thereof.

Aspect 15. The contact lens of any of aspects 11-14, wherein the cystine-sequestering material comprises gold nanoparticles.

Aspect 16. The contact lens of any of aspects 14-15, wherein the gold nanoparticles have an average size of about 10 nm-30 nm.

Aspect 17. The contact lens of any of aspects 14-15, wherein the gold nanoparticles have an average size of about 10 nm or less.

Aspect 18. The contact lens of any of aspects 14-17, wherein the loading of gold nanoparticles in the contact lens is about 5% or more.

Aspect 19. The contact lens of any of aspects 14-17, wherein the loading of gold nanoparticles in the contact lens is about 0.2%-10%

Aspect 20. The contact lens of any of aspects 11-19, wherein the lens base material is selected from hydroxyethyl methacrylate (HEMA), methacrylic acid, silicone-hydrogel, and combinations thereof.

Aspect 21. The contact lens of any of aspects 11-20, wherein the base material comprises methacrylic acid and hydroxyethyl methacrylate.

Aspect 22. The contact lens of aspect 21, wherein the base material comprises about 75% methacrylic acid and about 25% hydroxyethyl methacrylate.

Aspect 23. The contact lens of any of aspects 11-20, wherein the base material comprises about 100% methacrylic acid with small fraction of crosslinker to ensure mechanical strength.

Aspect 24. The contact lens of any of aspects 11-23, wherein the cystine-sequestering material comprises a combination of gold nanoparticles and methacrylic acid.

Aspect 25. The contact lens of any of aspects 11-24, wherein the contact lens comprises gold nanoparticles and thiolated acrylates.

Aspect 26. A method of making a disposable cystine-sequestering contact lens, the method comprising:
providing a pre-formed contact lens having a contact lens matrix or providing a contact lens base material precursor capable of forming a contact lens matrix;
providing a cystine-sequestering material selected from the group consisting of: gold nanoparticles, metallic nanoparticles capable of binding cystine, methacrylic acids, hydroxyethyl methacrylate, thiolated compounds, monomers of these compounds, combinations thereof, and precursors thereof;
combining the pre-formed contact lens or the contact lens base material with the cystine-sequestering material or precursors thereof; and
forming the disposable cystine-sequestering contact lens having the cystine-sequestering material within the contact lens matrix in an amount effective to uptake cystine from the eye of a patient.

Aspect 27. The method of aspect 26, wherein the pre-formed contact lens is a commercially available hydroxyethyl methacrylate lens (HEMA) or a silicone-hydrogel lens.

Aspect 28. The method of aspect 26 or 27, wherein the cystine-sequestering material comprises gold nanoparticles, and wherein the gold nanoparticles are formed in the pre-formed contact lens in situ by soaking the pre-formed lens in gold chloride followed by soaking the lens in a mixture of citric acid and gold chloride, whereby gold particles form within pores of the pre-formed lens.

Aspect 29. The method of aspect 28, wherein the gold chloride is chloroauric acid having a concentration of about 0.1-5% and wherein the citric acid has a concentration of 2-15 times the concentration of the gold chloride.

Aspect 30. The method of aspect 29, wherein the ratio of citric acid to chloroauric acid is from about 1 to 15.

Aspect 31. The method of any of aspects 28-30, wherein reduction of gold chloride to form the gold particles is achieved by reducing molecules loaded into the contact lens or integrated into the contact lens matrix.

Aspect 32. The method of aspect 26, wherein the contact lens base material precursor is a hydroxyethyl methacrylate (HEMA) monomer and wherein the method further comprises mixing the HEMA monomer with an aqueous phase comprising gold nanoparticles and a crosslinker, placing the mixture in a mold, and polymerizing the HEMA monomer to form a HEMA polymer matrix such that the gold nanoparticles are embedded in the HEMA polymer matrix.

Aspect 33. The method of aspect 32, wherein the gold nanoparticles have a concentration of about 1-5%.

Aspect 34. The method of any of aspects 32-33, wherein the crosslinker is ethylene glycol dimethacrylate (EGDMA).

Aspect 35. The method of any of aspects 32-34, further comprising, before polymerization, adding monomers selected from the group consisting of: thiolated methacrylates, tert butyl maethacrlate (tBM), methacrylic acid (MAA), hydroxyethyl methacrylate (HEMA), and combinations thereof.

Aspect 36. A method of treating cystinosis comprising: providing, for a patient in need of treatment for cystinosis, a disposable contact lens of any of aspects 11-25 with instructions to wear the contact lens in the eye of the patient for at least 8 hours/day, wherein the contact lens is effective to remove about 70 µg, or more, of cystine per day from the eye of the patient.

From the foregoing, it will be seen that aspects herein are well adapted to attain the ends and objectives hereinabove set forth together with other advantages which are obvious and which are inherent to the systems and methods.

It will be understood that certain features and subcombinations are of utility and may be employed without reference to other features and subcombinations. This is contemplated by and is within the scope of the aspects.

While specific elements and steps are discussed in connection to one another, it is understood that any element and/or steps provided herein is contemplated as being combinable with any other elements and/or steps regardless of explicit provision of the same while still being within the scope provided herein. Since many possible aspects may be made of the disclosure without departing from the scope thereof, it is to be understood that all matter herein set forth or shown in the accompanying drawings is to be interpreted as illustrative and not in a limiting sense

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1: Reaction of Cysteine with Gold Particles

Figure 5B:
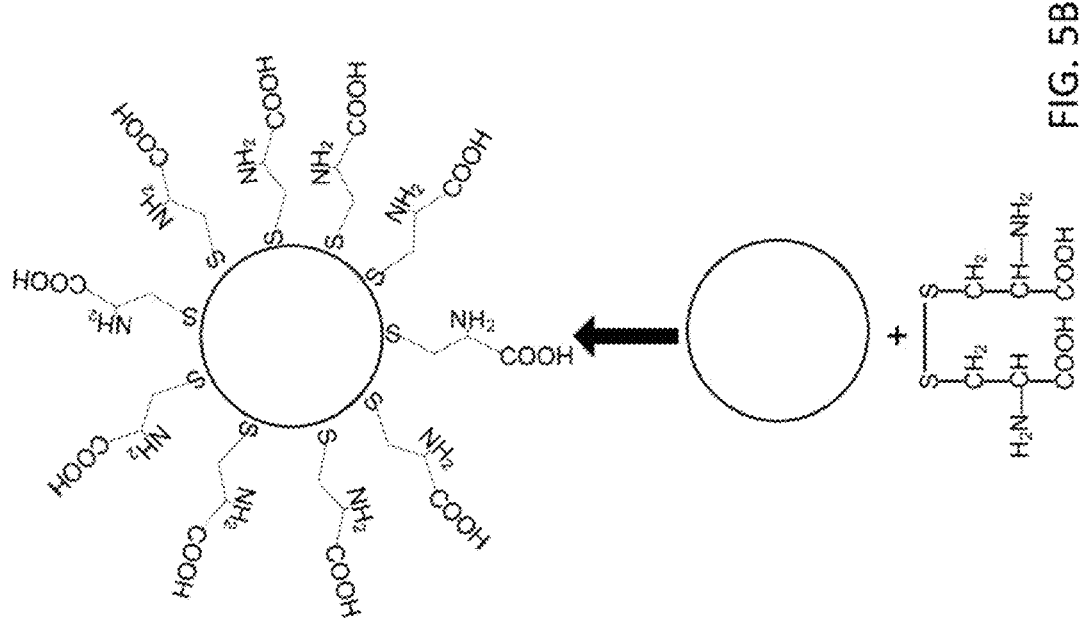
FIG. 5B shows a schematic of the reaction to illustrate that cystine splits into two molecules of cysteine during reaction and couples with the gold particle.
Figure 5A:
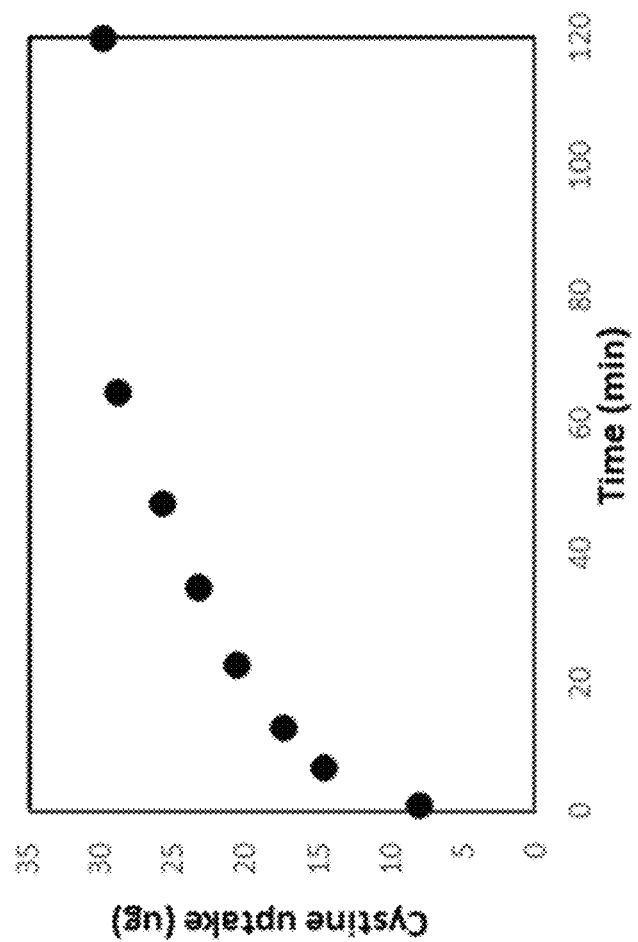
FIG. 5A illustrates the kinetics of cystine uptake by 25 nm gold nanoparticles.

A saturated solution of cystine in phosphate buffered saline—0.11 mg/mL—was mixed with equal part of gold nanoparticles (average diameter=25 nm) to give a final gold concentration of 170 µg/mL. Solution was measured by UV-spectrophotometry to determine the change in cystine concentration solution. The change in cystine mass is shown in FIG. 5A, with the result of approximately 30 µg of cystine adsorbed onto the gold nanoparticles. Cystine interaction with gold results in breakup of the disulfide bond and subsequent reaction of sulfur with gold as illustrated in the graphic shown in FIG. 5B. Many researchers have explored the structure and chemical composition of the sulfur-gold interface at the atomic level using both theoretical and experimental approaches. Yet efforts made using various sophisticated techniques have not resulted in a unifying picture of the sulfur-gold interface [Pensa, et al, 2012]. It is known though that the S—Au bond is stable with a high bond energy of 40-50 kcal/mol, which implies that the reaction of cystine on gold could be considered to be irreversible and will lead to a fully packed interface with an area per molecule of 130 Angstrom$^2$ at maximum packing [Hager, et al., 2003]. It is noted that cystine, which is the disulfide of cysteine, dissociated and reacts as cysteine, but the packing values are reported as equivalent cystine Example 2: Determining Optimum Cystine Capacity in a Contact Lens The present example describes the design of an embodiment of a contact lens in accordance with the present disclosure that can maximize the rate of cystine dissolution in the cornea and partitioning into the lens. With lenses with sufficiently high uptake capacity of cystine, the rate of cystine transport across the cornea will eventually limit the rate at which cystine can be removed. The rate of cystine transport through cornea into tears can be estimated as $kC_{sol}A_{cornea}$, where k is the permeability of the cystine through cornea, $C_{sol}$ (=0.1 mg/mL) is the solubility limit of cystine in stroma and $A_{cornea}$ (=1 cm$^2$) is the area of the cornea available for diffusion. This implicitly assumes that the concentration of cystine in the tears is zero, which would be the case if the rate of cystine transport through the cornea is the limiting step. The permeability k is unknown for cysteamine, but it typically ranges from $10^{-6}$ to $10^{-8}$ m/s [Waters, et al, 2003; Kotsmar, et al., 2012]. The epithelium permeability for timolol, a hydrophilic drug 316 Da MW is reported to be $1.2 \times 10^{-7}$ m/s. Considering that cystine will likely follow the same paracellular diffusion path as timolol and has a comparable molecular weight, the corneal permeability of cystine is predicted to be about $10^{-7}$ m/s [Prausnitz, et al., 2001; Prauznitz, et al., 1998]. As described below, the permeability will be measured using excised rabbit corneas, but here estimates were used for the preliminary calculations. Based on the permeability of $10^{-7}$ m/s, the rate of cystine across the cornea will be about 0.1 mg/day. Thus the goal is to provide a lens that has a total uptake capacity of about 0.2 mg of cystine because about 50% of the capacity could be used by cystine diffusing across the conjunctiva (see FIGS. 3 and 4). Most patients will wear the lens for only about 8 hrs a day, so that would reduce the need to only about 70 µg of cystine for each lens. It is also possible that the permeability in cornea is higher and patients may be willing to wear lenses for longer durations, and thus it could be useful to set a higher target at 200 µg of cystine.

Example 3: Design of a Gold Nanoparticle Loaded Contact Lens

To estimate the capacity of cystine in the lens, a gold nanoparticle loaded contact lens (GoldInLens™) of volume $V_{lens}$ loaded with gold particles of radius R and volume fraction is considered. The mass of cystine that can will react can on the surface of the gold particles be estimated as $$V_{lens} \varphi \frac{3}{R} \frac{MW}{N_{av}A}$$

where A° (=130 A$^2$/molecule) is the area per molecule at maximum packing and Nav and MW are the Avogadro number and molecular weight of cysteine, respectively. Based on these calculations, the time needed for the nanoparticles to fully react with cystine can be determined by the following equation:

$$V_{lens} \phi \frac{3}{R} \frac{MW}{N_{av}A} \frac{1}{kC_{sol}A_{cornea}}.$$

As an example, a 30 mg contact lens containing 1% 20 nm dia particles can react with 20 μm of cystine. If the particle loading is increased by a factor of 5, and the particle size is decreased to 10 nm, the uptake capacity will increase to 200 μg. Additional gains may be possible by creating even smaller particles in situ and/or improving partitioning of cystine in the lens.

Example 4: Comparing Efficacy of Gold-Containing Lens (GoldInLens™) with Eye Drop Therapy Based on the preliminary analysis shown above, it is possible to design a contact lens containing gold nanoparticles (GoldInLens™) that can remove about 100 μg of cystine from the cornea each day if the lens is worn 24 hr. Assuming that the patient uses only for 8 hr. each day, it would take about 5-10 months to react the 5-10 mg of cystine in stroma, which is significantly better compared to the current cystiamine drop therapy, which requires as long as a few years to clear already deposited crystals. After crystal dissolution, the needs of the therapy should decrease to remove the cystine that is continually deposited each day. Cysteamine eye drops used 4-times daily do not lead to any reduction of crystals, which suggests that the amount of cystine that is deposited every day needs about 4 drops of cysteamine. Patients are, however, prescribed the 8 drops a day regimen for their entire lives, even though, in principle, the drug needs should decrease after the crystals have dissolved. If the contact lenses are significantly superior, it may be possible to eventually reduce the lens use to just once weekly. This calculation implicitly assumes that the rate for of reaction on the surface of gold nanoparticles and the rate of cystine transport across the cornea is fast enough so that the surface of gold particles can be saturated within the wear duration of the lens. Preliminary data demonstrates that both reaction time and the time for cystine transport across the cornea are only a few hours, so these calculations represent reasonable estimates.

Figure 6:
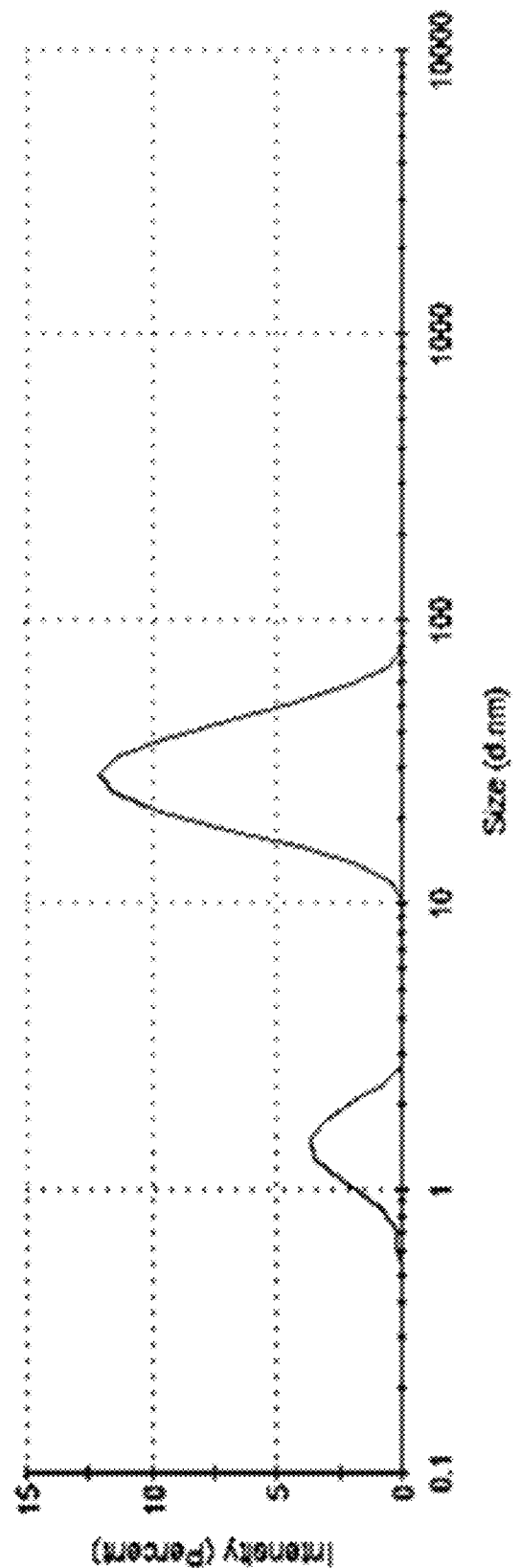
FIG. 6 illustrates DLS analysis of gold particles prepared by the Turkevich method and used for incorporation into the pHEMA lenses.

Example 5: Manufacturing Gold-Loaded Contact Lenses by Polymerizing Mixture of Gold Nanoparticles and Monomers A. Preparation of Gold Nanoparticles:

The Turkevich method is used to produce the gold particles by reducing chloroauric acid ($H[AuCl_4]$) with sodium citrate [Enustun, et al, 1963, incorporated by reference herein]. The citrate ions reduce $Au^{3+}$ to gold atoms that nucleate to form gold nanoparticles. The citrate ions also adsorb on the surface of the gold particles to act as capping agents preventing growth to larger sizes. Additional capping agents can be used to control the particle size. With this approach gold particles are prepared ranging in sizes from about 20 to 40 nm depending on the ratio of citrate to gold. The particle fraction obtained in this preparation depends on the starting concentration of the precursor chloroauric acid and is generally in 0.01% range and ratio of citrate is varied from one to three. Some researchers have produced particles with a higher starting concentration of the gold chloride and optimized citrate ion concentration [Zabetakis, et al, 2012]. The methods of Zabetakis et al. [2012, incorporated herein by reference] will be used, and the particle suspension will also be concentrated by evaporation to significantly higher values. A 5% loading in the lens is acheived by concentrating the gold solution either prior to or after addition to the monomer solution. Gold particles were prepared following the standard Turkevich method to obtain particles with a mean size of about 25 nm (FIG. 6). There was a smaller peak around 2 nm as well but the volume fraction under that peak is small (FIG. 6).

B. Incorporation of Particles into p-HEMA Lenses:

Gold nanoparticles (Au NP) have been incorporated in gels for a variety of applications including improving mechanical properties, controlled localized heating and thermo-switchable electrical properties. In these studies, gold nanoparticles or nanoshells were incorporated in a N-isopropylacrylamide/acrylamide polyacrylamide (PAAm) or NIPAAm) gel by swelling the dehydrated gel in the presence of Au—NP solution [Pardo-Yissar, et al., 2001] or by adding particles to a monomer mixture followed by polymerization [Zhao, et al., 2006; Sershen, et al., 2002, both of which are incorporated by reference herein]. Incorporation of gold particles in contact lens materials by swelling is not feasible because of the pore sizes are of the orders of a few nanometers. Commercial soft-contact lenses are either made from hydrogels such as hydroxyethyl methacrylate or silicone-hydrogels that include silicone monomers such as TRIS along with hydrophilic monomer such as HEMA along with a macromer that allows mixing of the silicone and the hydrophilic monomers.

The silicone-hydrogels are becoming preferred due to the high oxygen permeability, but there are still many hydrogel lenses in the market. Since the gold particles are prepared in the aqueous medium, gold particle-loaded hydrogel (HEMA) lenses are prepared by light initiated solution polymerization. 4 mL of aqueous phase containing gold particles at concentrations ranging from 1-5% is mixed with 6 mL of a mixture of HEMA monomer with 0.2% crosslinker ethylene glycol dimethacrylate (EGDMA) and 0.01% photo-initiator. The mixture is poured into either a contact lens mold or a glass mold that comprises of two plates separated by a 100 micron spacer, and polymerized under UV radiation for 40 min. Since the end product of the polymerization is a continuous film, the particles are trapped in the film.

Figures 7, 8:
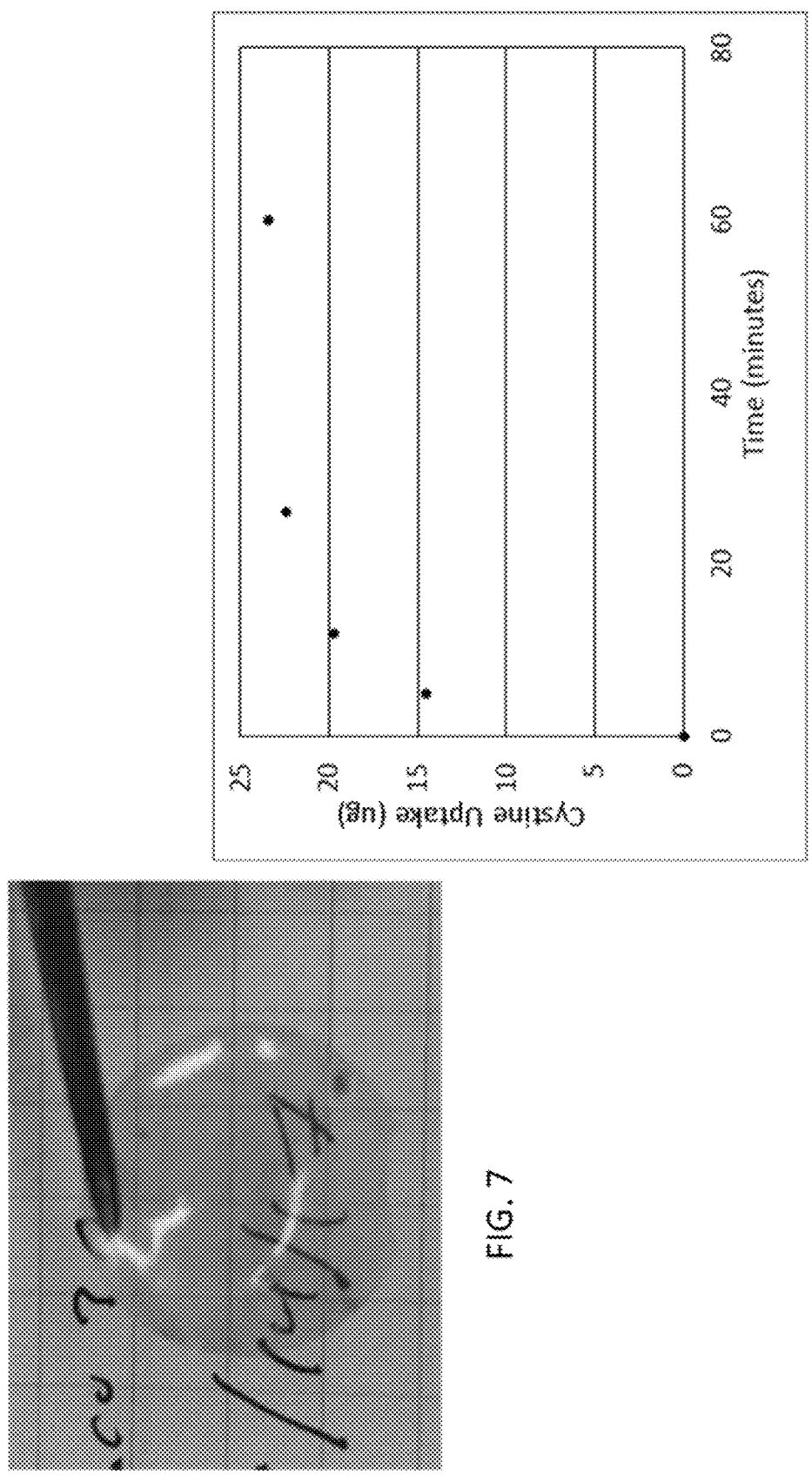
FIG. 7 is a digital image illustrating a 100 micron-thick pHEMA lens made with preformed gold nanoparticles (~25 nm diameter) added to monomer solution (0.5% gold concentration w/w FIG. 8 illustrates uptake of cystine by pHEMA lens made with preformed gold nanoparticles (~25 nm diameter) added to monomer solution (0.5% gold concentration w/w %).

The GoldInLens™ should be transparent and preferably colorless or only slightly colored, although there are potential benefits of colored lenses to cystinosis patients that suffer from photophobia. Gold nanoparticles (~30 nm) have a red color because the surface plasmon resonance phenomenon causes an absorption of blue-green light and reflection of the red light. The SPR is very sensitive is to the size of the particles but also the colloidal state of the suspension, whether it is isolated or coagulated. The plasmon band of coagulated particles shifts to a longer wavelength which can be visually observed as the color changes from red to blue-violet. Coagulation of the particles can be caused by a number of factors including salt addition or changes in solution conditions that reduce the zeta potential. Initial experiments show that addition of the HEMA monomer causes a color change, and furthermore the intensity of the color with 0.5% gold particles is low so a 100 μm thick film is transparent and almost colorless (FIG. 7).

C. Measuring Reaction of Cysteine with GoldInLens™:

The reaction of cystine with GoldInLens™ is measured by adding 30 mg of a flat gold-containing 100 micron thick pHEMA film to 3 mL of cystine solution, and following the reaction dynamics by periodically measuring the UV spectra of the solution. Dynamic UV spectra of the solution is measured to determine the cystine concentration in the solution, which 9 s then used to determine the concentration in gel. The measured concentration in the fluid is used to calculate the average concentration in the lens.

Cystine uptake was also measured in control pHEMA lenses without gold particles. The results showed 9.3 microgram of cystine uptake in 34 mg film. Thus the uptake of 25 microgram in the gold loaded pHEMA film can be due to a combination of 9.3 microgram of cystine adsorbed on the pHEMA gel and 15.7 microgram of cystine on the surface of the gold particles. Based on estimates of 130 Angstrom, 2 per molecule of cystine coverage, about 10-12 microgram of cystine is expected on the surface of gold particles (FIG. 8).

Example 6: Manufacturing Gold Particle Loaded Lenses by In Situ Formation of Gold Nanoparticles in the Lenses Since cystine reacts with gold only on the surface of the particles, a reduction in the size of the gold particles is desirable. Researchers have explored the Brust-Schiffrin method for preparing smaller nanoparticles compared to those obtained by the Petrovich [Waters, et al., 2003, which is incorporated herein by reference]. This approach however uses organic solvents which would make eventual lens preparation difficult. The present example uses an alternate approach of using the pores in the contact lenses to control the particle size. Essentially, this approach uses the nanopores in the contact lens matrix as the scaffolds to obtain particles that are potentially as small as 2-4 nm for some contact lenses [Kotsmar, et al., 2012; Bengani, et al., 2012]. Another benefit of this approach compared to addition of gold particles prior to polymerization is the flexibility of using any material including silicone hydrogel based contact lenses. Since silicone is not compatible with aqueous solutions, the first approach cannot be used to incorporate particles in the silicone hydrogels. Using a similar approach, Gema, M. et al. created acrylamide-NIPAAm hydrogels loaded with gold nanoparticles [Marcelo, et al., 2014]. The microstructure of the gold particles in the contact lenses is significantly different compared to the acrylamide-NIPAAm for various reasons, including significant differences in pore sizes.

Figure 9:
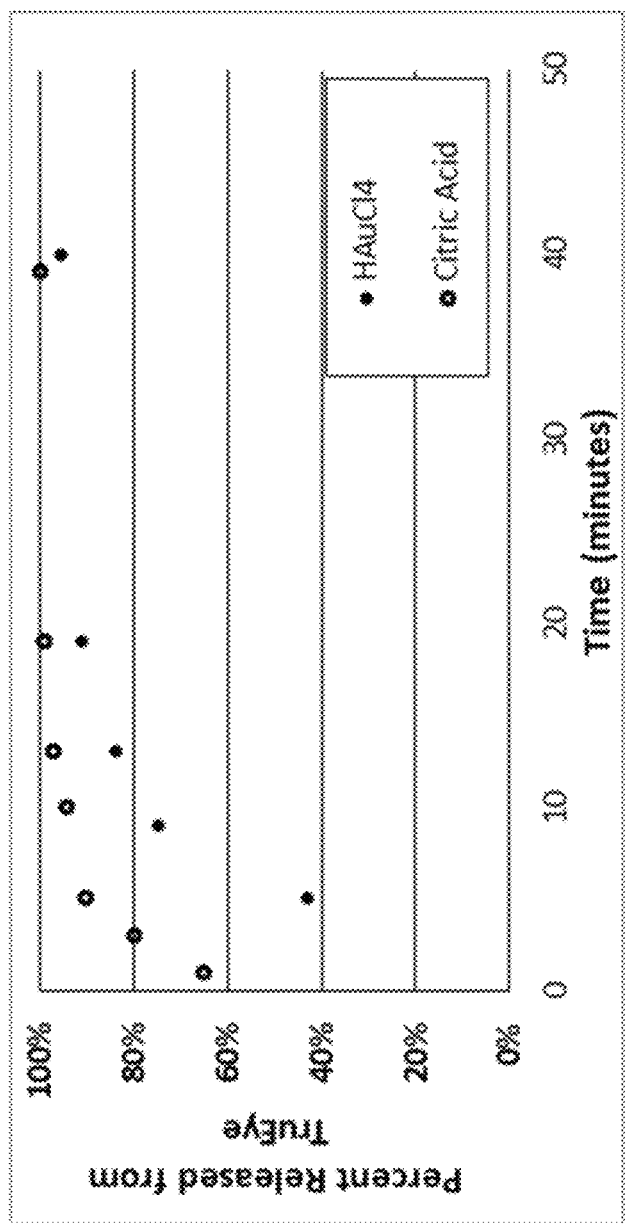
FIG. 9 is a graph illustrating release of chloroauric acid and citric acid from TRUEYE® (available from Johnson & Johnson, New Brunswick, NJ, US) (Narafilcon A) contact lens.

A. Measuring Transport of Gold Precursor and Citric Acid into the Contact Lenses:

The diffusion of molecules will play a critical role so this example measures the diffusivity and partition coefficients of chloroauric acid and citric acid. Pre-formed contact lenses are soaked in 3 mL of precursor solution of chloroauric acid for 4 hours to ensure that the concentration inside the lens is in equilibrium with the bulk concentration. Next, the loaded lenses are placed in PBS and the dynamic spectra is measured to determine the mass of chloroauric acid released as a function of time. The release data is then fitted to a diffusion control model to determine diffusivity and partition coefficient (FIG. 9). The same approach is used to determine diffusivity and partition coefficient for citric acid. These studies were performed with Acuvue TRUEYE® (Narafilcon A) lens to obtain the following results:

The release studies show that the release and uptake durations are less than 30 minutes. The partition coefficients for TRUEYE® (Narafilcon A) are:

|  | K (HAuCl4) | K (Citric Acid) |
| --- | --- | --- |
| TruEye | 3.71 | 0.4 |

B. Experiment Methods for Preparing Gold Particle-Loaded Lenses by In Situ Approach:

This example involves soaking the gel (~30 mg in weight) in 3 mL chloroauric acid until equilibrium is achieved. Next, the gel is soaked in 3 mL citric acid containing chloroauric acid at the same concentration as in the first step to ensure that there is no net loss of the gold precursor. The lenses are removed from the solution after citric acid has diffused into the lens, and transferred to a humidified chamber to ensure that there is no loss of any of the components to the solution, and the lens remains fully hydrated. Alternatively the lens can remain soaked in the mixture of citric acid and chloroauric acid until the reaction is complete, which is expected to take a few hours.

C. Measuring Cystine Uptake and Other Relevant Properties:

To test the cystine uptake capacity, the gold loaded gel is added to 3 mL 0.05-1 mg/ml cystine solution, and the dynamics of cystine consumption is followed to determine the mass of reaction that reacts with gold. Using the area per molecule of 130 Angstrom$^2$ at maximum packing, the total surface area of gold aggregates is calculated. The mass of gold in the lens is determined from the mass of chloroauric acid loaded, and used to determine the characteristic length scale for the gold aggregates as $$\frac{\text{Mass of gold}}{\rho_{Gold}(\text{Surface Area})}.$$

For a sphere, this number is one third of the radius.

Additionally, the UV-Vis spectra of the particle loaded lens is also measured. The wavelength of maximum absorption at least qualitatively indicates the size of the aggregates. The lens is also imaged by SEM to get direct evidence of the microstructure of the gold aggregates, and FTIR and Raman are used on the lens after reaction with cystine to get further evidence of the reaction. Finally, the gold-loaded lens (GoldInLens™) is soaked in ethanol to swell the lens to about 9 times by volume which would possibly release a large fraction of the loaded particles. UV vis analysis and dynamic light scattering is used to determine the size and concentration, which is then compared with results obtained by other approaches for length scale and gold loading in the lens. Also, UV vis spectra of the lens will be measured after extraction to determine whether there are remaining particles inside. For the high gold loadings (>0.5%) the gain in dry weight is also measured as another method for determining the gold particle loading. This experimental scheme is used to explore the impact of pore size, partition coefficient, and concentration of chloroauric acid and citrate/gold ratio in the lens on microstructure and more specifically on for the on the length scale of the aggregates.

Figure 10:
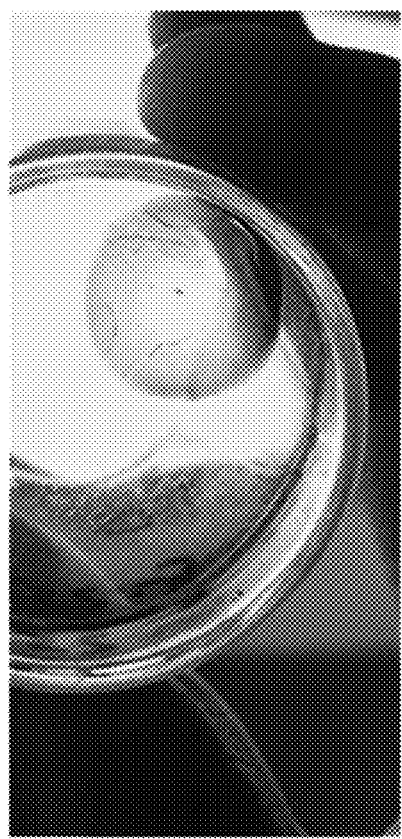
FIG. 10 is a digital image illustrating TRUEYE® (Narafilcon A) made in-situ with 1% $HAuCl_4$ and 10% Citric acid.
Figure 11:
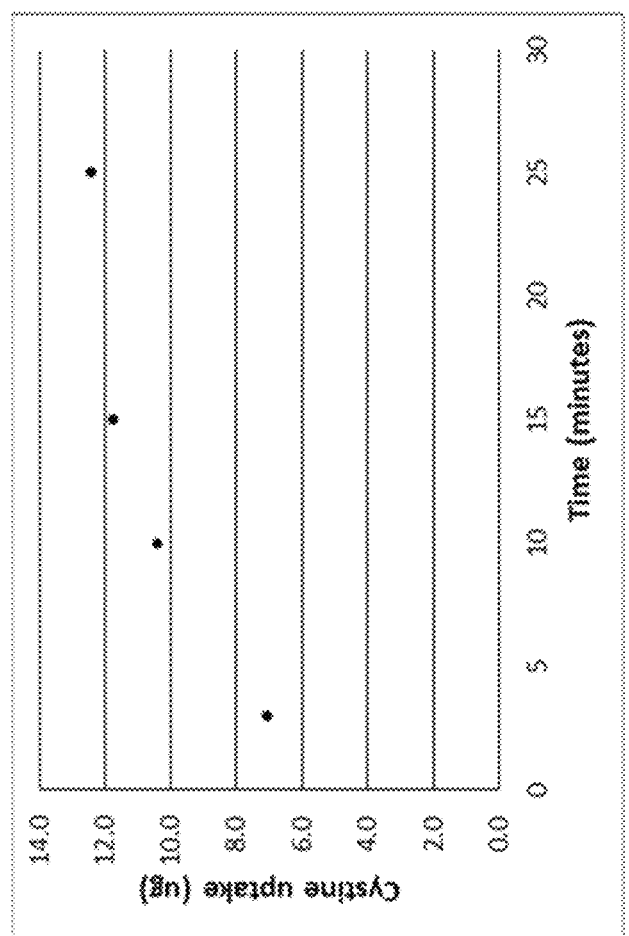
FIG. 11 illustrates uptake of cystine by TRUEYE® (Narafilcon A) made in-situ with 1% $HAuCl_4$ and 10% Citric acid.

This study was performed on a commercial contact lens Acuvue TRUEYE® (Narafilcon A). The TRUEYE® (Narafilcon A) lens was soaked in 1% gold chloride solution. After loading was complete, the external solution was replaced by 1% gold chloride and 10% citric acid. The lens was removed from the solution after about 30 min (FIG. 10). The cystine uptake was then measured by soaking the gold loaded Acuvue TRUEYE® (Narafilcon A) in cystine solution (FIG. 11).

The reaction of gold chloride and citric acid was likely not completed by the time the lens was removed. The mass of gold and hence the mass of cystine that reacts can be increased by allowing the gold particle formation to last longer, preferably until completion which may take about 24 hours.

Figure 12:
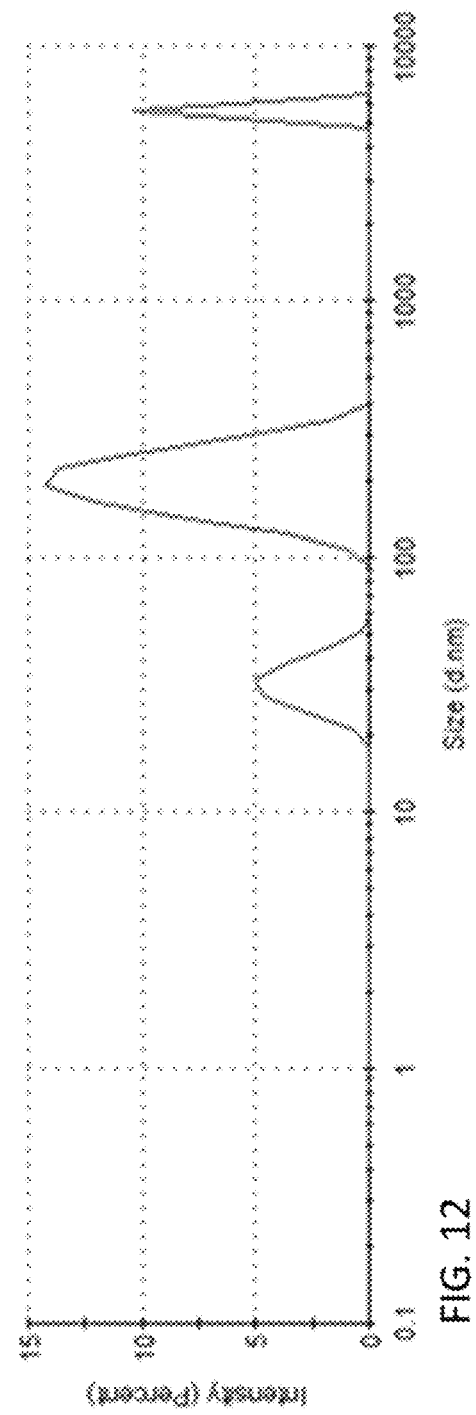
FIG. 12 is a DLS analysis of particles that came out of the gold loaded TRUEYE® (Narafilcon A) lenses prepared by the in situ approach by soaking in ethanol. The larger size particles may be aggregates.
Figure 13:
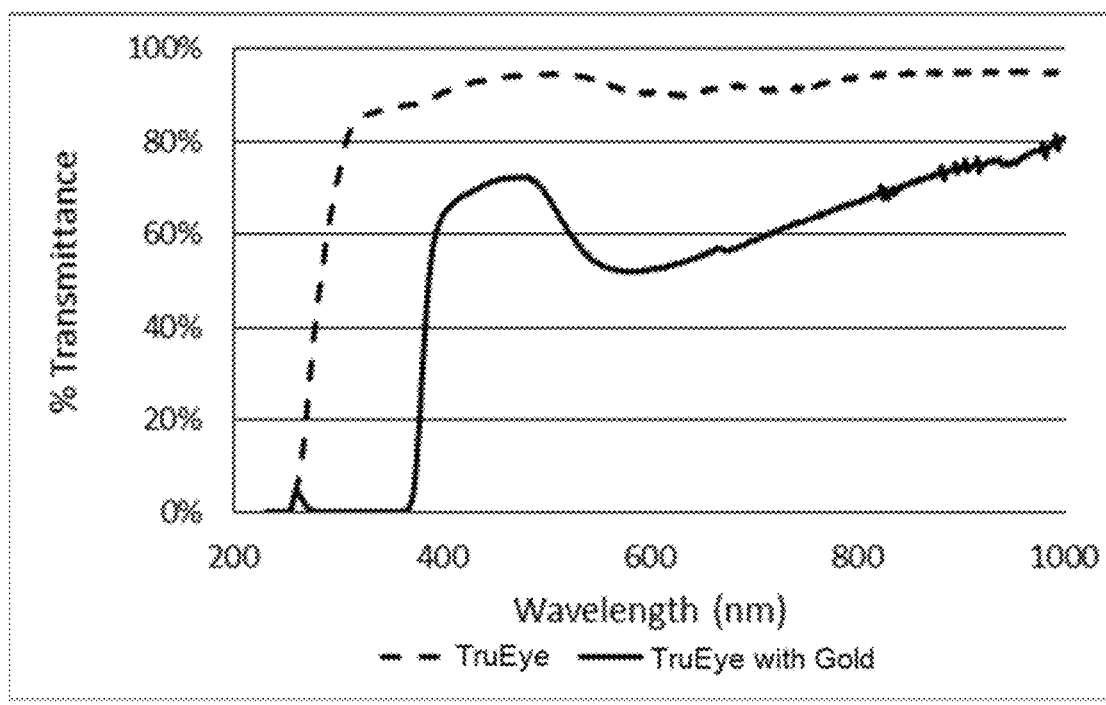
FIG. 13 illustrates transmittance comparison of TRUEYE® (Narafilcon A) contact lens with and without in-situ gold loading.

To determine the size of gold particles that form inside the TRUEYE® (Narafilcon A) lens the lens loaded with particles was soaked in ethanol. The lens swelled significantly in ethanol releasing the particles. The size distribution of the released particles was measured using dynamic light scattering. About 10-20 nm size particles and larger particles that are likely aggregates were observed (FIG. 12). Also transmittance spectra of the lens was measured and compared with the control lens (FIG. 13).

D. Effect of Pore Size:

Discrete gold particles of size similar to that in bulk will be dispersed uniformly in the matrix if the pore size is larger than the diameter. For small pore sizes, the confinement of the pore leads to formation of particles that are comparable in size to the pore. It is however possible that fluctuation in the pore sizes allows the pores to be enlarged due to the formation of the gold particles. It is also possible to obtain a more complex microstructure including smaller particles in pores connected by channels. The pore size in a gel can be related to the gel rheology through the following equation [Bengani, et al., 2012, which is hereby incorporated by reference herein]:

$$\xi = l_{c-c}\left(\frac{6C_n\rho_2 RT}{EM_r\phi_2^{1/3}}\right)^{1/2} = l_{c-c}\left(\frac{2C_n\rho_2 RT}{G'(\omega=0)M_r\phi_2^{1/3}}\right)^{1/2} \quad (7)$$

where $l_{c-c}$ is the length of a covalent carbon-carbon bond in the backbone (1.54 Å for HEMA gel), $C_n$ is the Flory characteristic ratio or rigidity factor (6.9 for p-HEMA gels) [Guan, et al., 2011, which is hereby incorporated by reference herein], $\rho_2$ is the mass density of dry polymer (1.26 g/ml), $M_r$ is the molecular wt. of a repeat unit (130 g/mol in this case) [Guan, et al., 2011], E is the Young's tensile modulus, $\varphi_2$ is the polymer fraction in a swollen gel and is gel mesh size, defined as the statistical length between two crosslinks, and $E=2G'(1+v)$ where G' is storage modulus that can be measured through dynamic rheology measurements and Possion's ratio $v=0.5$ for incompressible gels. By varying the ratio of crosslinker in the HEMA gel gels are prepared with pore sizes ranging from 1-5 nm. Larger pores are obtained by addition to a chain termination agent that reduces the chain length and minimizes chain transfer reactions. Further increases in pore size are obtained by addition of a more hydrophilic monomer to the gel such as dimethyl acrylamide. Gels of various degrees of crosslinkings are obtained and measured for dynamic rheology using a Dynamic Mechanical Analyzer to obtain the pore size. Gels with pore sizes ranging from 2 to 20 nm are obtained.

E. Effect of Gold Concentrate and Citrate/Gold Ratio:

The concentration of gold in the lens and the citrate/gold ratio plays an important role, so both of these are varied in the lens. By using the known partition coefficient of both components in the lens, experiments are conducted for ratio of citrate to gold ranging from one to five and chloroauric acid concentrations from 0.5-5% w/w. The experiments described above are also conducted to explore a range of pore sizes and explore the dependency of microstructure on the pore size.

F. Multiple Reaction Cycles:

Multiple cycles of gold loading will also be explored, i.e., forming the gold particles in the lens, followed by soaking in chloroauric acid and reduction by citric acid to increase the loading of gold. It is envisioned that the rate of particle formation in the second cycle will be faster because the particles from the previous cycle may form sites for deposition.

G. Types of Lenses Used for In Situ Approach:

Based on the results from the fundamental studies described above conditions can be chosen that maximize the cystine uptake with the overall goal of designing a lens with an uptake capacity of at least 70 µg, and if feasible, 200 µg. Gold structures will be incorporated in a number of different contact lenses materials including the following:

| Group 1-Low Water (<50% H20) Nonionic Polymers | | | |
|---|---|---|---|
| Material | % Water | Oxygen Permeability (Dk) | Brands |
| Teflicon | 38 | 8.9 | Cibasoft, Illusions, Torisoft |
| Tetrafilcon A | 43 | 9 | CooperToric, Preference, Preference Toric, Vantage |
| Crofilcon | 38 | 13 | CSI, CSI Toric |
| Hefilcon A | 45 | 12 | |
| Hefilcon B | 45 | 12 | |
| Mafilcom | 33 | 4 | |
| Polymacon | 38 | 9 | Biomedics 38, Edge III, Z4/Z6, Soflens 38 |
| Hioxifilcon B | 49 | 15 | Alden SE |
| Galyfilcon A | 47 | 86[14] | Acuvue Advance with Hydraclear, Advance for Astigmatism |
| Lotrafilcon A | 24 | 140 | Focus Night & Day |
| Lotrafilcon B | 38 | 140 | O2Optix/AirOptix |
| Senofilcon A | 38 | 107 | Acuvue Oasys |
| Samfilcon A | 46[15] | 163[16] | Bausch + Lomb Ultra |

| Group 2-High Water (>50% H20) Nonionic Polymers | | | |
|---|---|---|---|
| Material | % Water | Oxygen Permeability (Dk) | Brands |
| Surfilcon A | 74 | 35 | |
| Lidofilcon A | 70 | 31 | |
| Lidofilcon B | 79 | 38 | |
| Netrafilcon A | 65 | 34.5 | |
| Hefilcon C | 57 | ? | |
| Alfafilcon A | 66 | 32 | Soflens 66 |
| Omafilcon A | 59 | 33 | Proclear Compatibles |
| Vasurfilcon A | 74 | 39.1 | |
| Hioxifilcon A | 59 | 36 | Definity 59%, Aura ADM |
| Hioxifilcon D | 54 | 21 | Definity 54% |
| Nelfilcon | 69 | 26 | Focus Dailies, Dailies Toric |
| Hilafilcon A | 70 | 35 | Soflens 1-day |
| Hilafilcon B | 59 | 22 | Soflens 59 |

| Group 3-Low Water (<50% H20) Ionic Polymers | | | |
|---|---|---|---|
| Material | % Water | Oxygen Permeability (Dk) | Brands |
| Balafilcon A | 36 | 112/130 | Purevision, Purevision 2 |
| Bufilcon A | 45 | 16 | |
| Deltafilcon A | 43 | 10 | |
| Phemfilcon | 38 | 9 | Durasoft 2 |

Group 4-High Water (>50% H2O) Ionic Polymers

| Material | % Water | Oxygen Permeability (Dk) | Brands |
| --- | --- | --- | --- |
| Bufilcon A | 55 | 16 | |
| Perfilcon A | 71 | 34 | |
| Etafilcon A | 58 | 28 | Acuvue, Acuvue Bifocal, Acuvue 2, Acuvue 1-day |
| Focofilcon A | 55 | 16 | |
| Ocufilcon B | 53 | 16 | |
| Ocufilcon C | 55 | 16 | |
| Ocufilcon D | 55 | 19.7 | Biomedics 55, Biomedics 55 Premier |
| Ocufilcon E | 65 | 2 | |
| Ocufilcon F | 60 | 24.3 | |
| Phemfilcon A | 55 | 16 | Durasoft 3, Freshlook, Wildeyes |
| Methafilcon A | 55 | 18 | Sunsoft Eclipse, Revolution, Sunsoft Toric |
| Methafilcon B | 55 | 18 | Frequency 55 Toric |
| Vilfilcon A | 55 | 16 | Focus 1-2 Week, Focus Toric, Focus Progressives |

Example 7: Optimization of Partition Coefficient of Cystine in the Contact Lens Matrix This example focuses on optimizing the monomer composition of the lenses to increase cystine uptake by adsorption on the polymer matrix. Monomers are incorporated that can increase binding of cystine to increase the partition coefficient fox example methacrylic acid exhibits binding to cystine through interaction of carboxylic acid. By combining both gold loading and improved partitioning in the lens, the cystine uptake capacity can be further increased to achieve the target. If greater cystine capacity is still desired, incorporation of thiolated methacrylates into the gels can also be conducted to allow for direct reaction between cystine and the thiol group. However, since this approach may result in loss of activity due to reaction with oxygen both during storage and wear, in the present example, the partition coefficient was measured in lenses prepared by mixing various monomer components including tert butyl maethacrlate (tBM), methacrylic acid (MAA) and hydroxyethyl methacrylate (HEMA)

| Gel Formulation | K (cystine) |
| --- | --- |
| 75%/25% p-tBM/MAA | 1.16 ± 0.11 |
| p-H EMA | 2.72 ± 0.12 |
| 75%/25% p-MAA/HEMA | 11.17 ± 0.39 |
| pMAA | 19.59 ± 0.98 |

From the results, it was discovered that poly(MAA) gels have high affinity for cystine. In fact. MAA gels 19.5 mg in weight take about 55 microgram of cystine without incorporation of gold particles. The uptake increases to 86.1 microgram when gold particles are incorporated by soaking the MAA gel in 1% gold chloride, followed by 1% gold chloride and 10% citric acid for about an hour. Cystine uptake may further increase if the reaction is allowed to proceed to completion.

| Formulation | Allowed reaction time | Cystine uptake (µg) |
| --- | --- | --- |
| pHEMA with gold (in-situ) | ~1 hr | 30.1 |
| | overnight (~15 hrs) | 49.8 |
| TruEYE with gold (1% HAuCl4) | ~1 hr | 11.7 |
| pMAA with gold (in situ) | overnight (~15 hrs) | 17.3 |
| | ~1 hr | 86.1 |
| | overnight (~15 hrs) | 94.8 |

Figure 14:
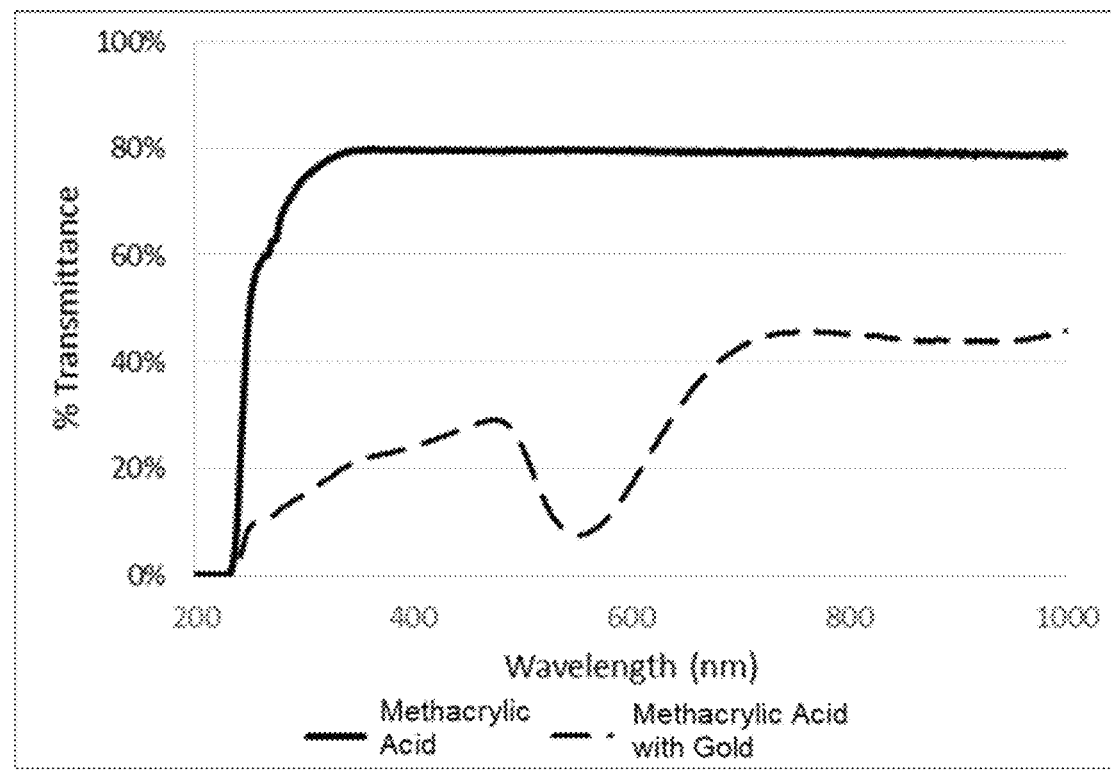
FIG. 14 illustrates transmittance comparison of pMAA gel with and without in-situ gold loading.
Figure 15:
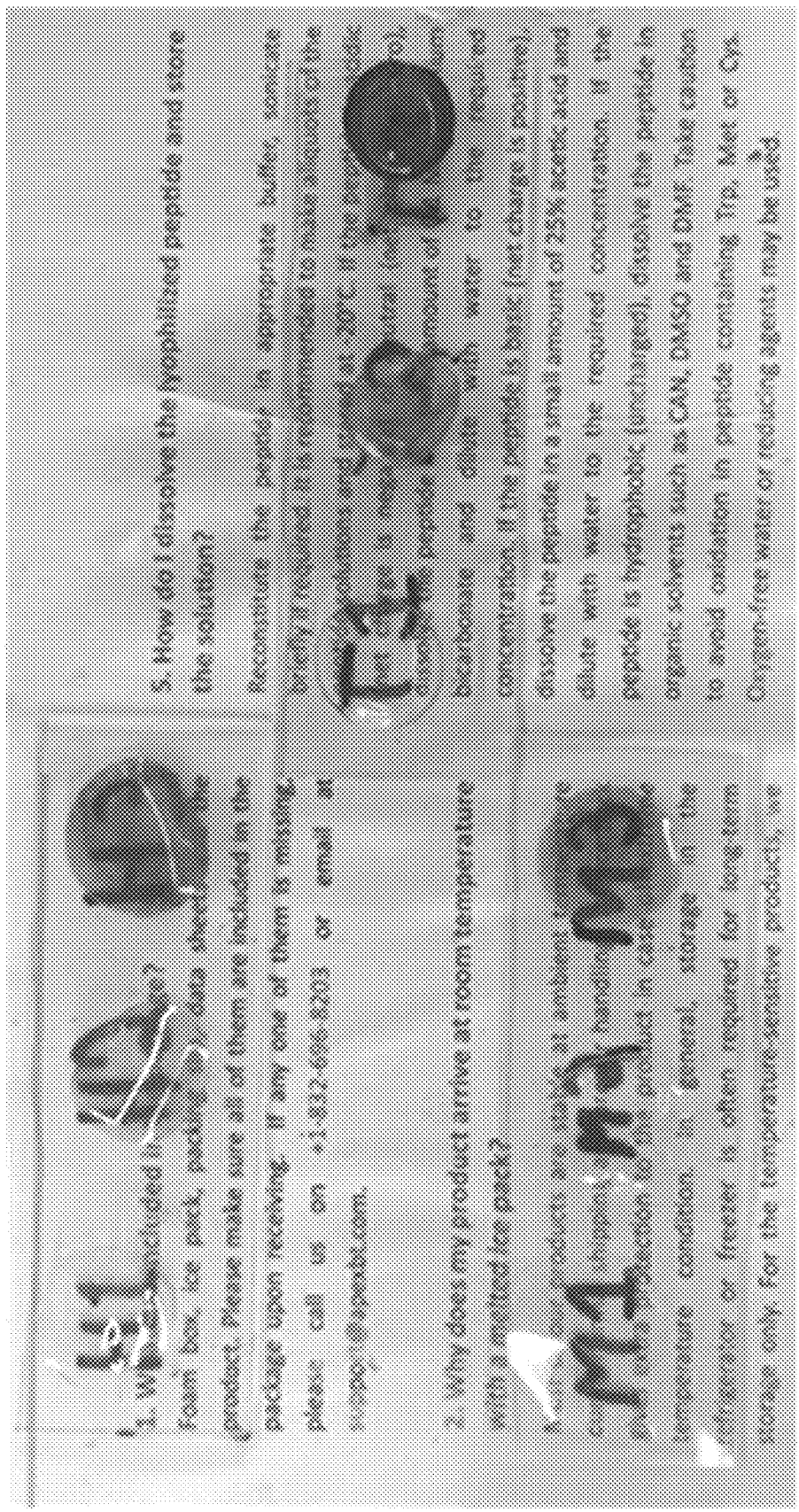
FIG. 15 is a digital image illustrating dried gels and lenses made according to embodiments of the present disclosure, with and without gold particles. Top row, left to right: H1-pHEMA gel, H2-pHEMA with gold in monomer solution, H3: pHEMA with in-situ gold; middle row, left to right: T1: ACUVUE® TRUEYE® (Narafilcon A), T2: TRUEYE® (Narafilcon A) with 0.5% gold chloride in-situ, T3: TRU- EYE® (Narafilcon A) with 1% gold chloride in-situ; Bottom row, left to right: M1: pMAA gel, M2: pMAA with gold in monomer solution.

FIG. 14 shows a comparison of transmittance of pMAA gel with vs without in-situ gold loading. For these experiments, the in situ gels were prepared by using 1% gold chloride and 10% citric acid. Particle formation process was terminated after only about an hour. For direct incorporation, 0.5% (w/w) 25 nm size particles were added to the monomer mixture. Below is a summary of the mass of cystine uptake by the various materials, both with and without gold, and FIG. 15 shows images of dried gels and lenses with and without gold particles (made by direct incorporation or in situ).

| Formulation | Gel mass (mg) | Cystine uptake (µg) |
| --- | --- | --- |
| pHEMA | 34.7 | 9.3 |
| pHEMA with gold (monomer soluton) | 31.5 | 23.4 |
| pHEMA with gold (in-situ) | 37.1 | 30.1 |
| TruEYE | 23.6 | 2.6 |
| TruEYE with gold (0.5% HAuCl$_4$) | 23.4 | 7.8 |
| TruEYE with gold (1% HAuCl$_4$) | 23.8 | 11.7 |
| pMAA | 19.5 | 55.0 |
| pMAA with gold (monomer solution) | 20.2 | 62.1 |
| pMAA with gold (in-situ) | 23.1 | 86.1 |

REFERENCES

1. Pensa E, Cortes E, Corthey G, Carro P, Vericat C, Fonticelli M H, Benitez G, Rubert A A, Salvarezza R C, The Chemistry of the Sulfur-Gold Interface: In Search of a Unified Model, Accounts of Chemical Research, 2012, 45 (8), 1183-1192.
2. Hager G, Brolo A G, Adsorption/desorption behaviour of cysteine and cystine in neutral and basic media: electrochemical evidence for differing thiol and disulfide adsorption to a Au(1 1 1) single crystal electrode, Journal of Electroanalytical Chemistry, 2003, 550/551, 291-301.
3. Edward A, Prausnitz M R, Predicted permeability of the cornea to topical drugs, Pharm Res, 2001, 18(11), 1497-1508.
4. Prausnitz M R, Noonan J S, Permeability of cornea, sclera, and conjunctiva: a literature analysis for drug delivery to the eye, J Pharm Sci, 1998, 87(12), 1479-1488.
5. Enüstün B V, Turkevich J, Coagulation of colloidal gold, J. Am. Chem. Soc., 1963, 85, 3317-3328
6. Zabetakis K, William E G, Kumar S, Daniel M C, Effect of high gold salt concentrations on the size and polydispersity of gold nanoparticles prepared by an extended Turkevich-Frens method, Gold Bulletin, 2012, 45(4), 203-211.
7. Pardo-Yissar, V, Gabai, R, Shipway, AN, Bourenko T, Willner I, Gold Nanoparticle/Hydrogel Composites with Solvent-Switchable Electronic Properties. Adv. Mater., 2001, 13 1320-1323

8. Zhao X, Ding X, Deng Z, Zheng Z, Peng Y, Tian C, Long N J, A kind of smart gold nanoparticle-hydrogel composite with tunable thermo-switchable electrical properties, New Journal of Chemistry, 2006, 30, 915-920.
9. Sershen S R, Westcott S L, Halas N J, West J L, Independent optically addressable nanoparticle-polymer optomechanical composites, Appl. Phys. Lett., 2002, 80, 4609-4612.
10. Waters C A, Mills A J, Johnson K A, Schiffrin D J, Purification of dodecanethiol derivatised gold nanoparticles, Chem. Commun., 2003, 4, 540-541.
11. Kotsmar C, Sells T, Taylor N, Liu D E, Prausnitz J M, Radke C J, Aqueous Solute Partitioning and Mesh Size in HEMA/MAA Hydrogels, Macromolecules, 2012, 45, 9177-9187.
12. Bengani L C, Leclerc J, Chauhan A, Lysozyme transport in p-HEMA hydrogel contact lenses, Journal of Colloid and Interface Science, 2012, 386, 441-450.
13. Marcelo G, López-González M, Mendicuti F, Tarazona M P, Valiente M, Macromolecules, 2014, 47, 6028-6036.
14. Guan, L, Gonzalez-Jimenez M E, Walowski C, Boushehri A, Prausnitz J S, Radke C J, J. Appl. Poly. Sci., 2011, 121, 1457-1471.

GENERAL REFERENCES

15. Bradbury J A, Danjoux J P, Voller J, Spencer M, Brocklebank T, A randomised placebo-controlled trial of topical cysteamine therapy in patients with nephropathic cystinosis. Eye (London), 1991, 5(6), 755-760.
16. Jain S, Kuwabara T, Gahl W A, Kaiserkupfer M I, Range of toxicity of topical cyteamine in rabbit eyes. Journal of Ocular Pharmacology, 1988, 4(2), 127-131.
17. Li C, Chauhan A, Modeling ophthalmic drug delivery by soaked contact lenses, Ind Eng Chem Res, 2006, 45(10), 3718-3734.
18. Hsu K—H, Fentzke R C, Chauhan, A, Feasibility of Corneal Drug Delivery of Cysteamine Using Vitamin E Modified Silicone-hydrogel Contact Lenses, European Journal of Pharmaceutics and Biopharmaceutics, 2013, 85(3 Pt A), 531-540.
19. Chauhan A, Kim J, "Contact Lenses for extended release of bioactive agents containing diffusion attenuators", U.S. Pat. No. 8,404,265.
20. Hsu K—H, Lazon de la Jara P, Ariyavidana A, Watling J, Holden B, Garrett A, Chauhan A, Release of Betaine and Dexpanthenol from Vitamin E Modified Silicone-hydrogel Contact Lenses, Curr Eye Res, 2015, 40(3), 267-273.
21. Hsu K—H, Gause S, Chauhan, A, Review of Ophthalmic Drug Delivery by Contact Lenses, Journal of Drug Delivery Science and Technology, 2014, 24(2), 123-135.
22. Bengani L, Hsu K—H, Gause S, Chauhan A, Contact lenses as a platform for ocular drug delivery, Expert Opinion on Drug Delivery, 2013, 10(11), 1483-1496.
23. Hsu K—H, Fentzke R C, Chauhan, A, Feasibility of Corneal Drug Delivery of Cysteamine Using Vitamin E Modified Silicone-hydrogel Contact Lenses, European Journal of Pharmaceutics and Biopharmaceutics, 2013, 85(3 Pt A), 531-540.
24. Peng C C, Burke, MT, Chauhan, A, Transport of Topical Anesthetics in Vitamin E Loaded Silicone Hydrogel Contact Lenses, Langmuir, 2012, 28(2), 1478-1487.
25. Peng C C, Chauhan A, Extended Cyclosporine Delivery by Silicone-Hydrogel Contact Lenses, Journal of Controlled Release, 2011, 154, 267-274.
26. Kim J, Peng C C, Chauhan A, Extended delivery of dexamethasone from silicone-hydrogel contact lenses containing Vitamin E diffusion barriers, Journal of Controlled Release, 2010, 148, 110-116.
27. Peng C C, Kim J, Chauhan A, Extended delivery of hydrophilic drugs from silicone-hydrogel contact lenses containing Vitamin E diffusion barriers, Biomaterials, 2010, 31 (14), 4032-4047.
28. Peng C C, Burke M T, Carbia B E, Plummer C, Chauhan A, Extended Drug Delivery by Contact Lenses for Glaucoma Therapy, Journal of Controlled Release, 2012, 162 (1), 152-15.
29. Jaenen N, Baudouin C, Pouliquen P, Manni G, Figueiredo A, Zeyen T, Ocular symptoms and signs with preserved and preservative-free glaucoma medications, European journal of ophthalmology, 2007, 17, 341-349.
30. Ishibashi T, Yokoi N, Kinoshita S, Comparison of the short-term effects on the human corneal surface of topical timolol maleate with and without benzalkonium chloride, Journal of glaucoma, 2003, 12, 486-490.
31. Zhanfang M, Hongliang H, One-step synthesis of cystine-coated gold nanoparticles in aqueous solution, Colloids and Surfaces A: Physicochem. Eng. Aspects, 2008, 317, 229-233.
32. Sershen S R, Westcott S L, Halas N J, West J L, Independent optically addressable nanoparticle-polymer optomechanical composites, Appl. Phys. Lett., 2002, 80, 4609-4612.
33. Wu X, Pelton R H, Hamielec A E, Woods D R, McPhee W, The kinetics of poly (N-isopropylacrylamide) microgel latex formation, Colloid Polym Sci, 1994, 272, 467-477.
34. Marcelo G, López-González M, Mendicuti F, Tarazona M P, Valiente M, Macromolecules, 2014, 47, 6028-6036.
35. Pong B K, Elim H I, Chong J X, Ji W, Trout B L, Lee J Y, New Insights on the Nanoparticle Growth Mechanism in the Citrate Reduction of Gold(III) Salt: Formation of the Au Nanowire Intermediate and Its Nonlinear Optical Properties, The Journal of Physical Chemistry C, 2007, 111 (17), 6281-6287.
36. Polte J, Ahner T T, Delissen F, Sokolov S, Emmerling F, Thünemann A F, Kraehnert R, Mechanism of Gold Nanoparticle Formation in the Classical Citrate Synthesis Method Derived from Coupled In Situ XANES and SAXS Evaluation, Journal of the American Chemical Society, 2010, 132 (4), 1296-1301.

The invention claimed is:
1. A method of making a disposable cystine-sequestering contact lens, the method consisting of:
providing a pre-formed contact lens having a contact lens matrix;
providing a cystine-sequestering material, wherein the cystine-sequestering material consists of gold nanoparticles, and wherein the gold nanoparticles are formed in the pre-formed contact lens in situ by soaking the pre-formed lens in a gold chloride followed by soaking the lens in a mixture of citric acid and gold chloride, wherein the gold chloride is chloroauric acid, whereby gold particles form within pores of the pre-formed lens;
forming the disposable cystine-sequestering contact lens having the cystine-sequestering material within the contact lens matrix in an amount effective to uptake cystine from the eye of a patient; wherein a partition coefficient for the chloroauric acid within the contact lens is about 3.71 relative to a concentration of chloroauric acid in the mixture of citric acid and gold chloride, and wherein method steps are performed in order as listed.

2. The method of claim 1, wherein the pre-formed contact lens is a commercially available hydroxyethyl methacrylate lens (HEMA) or a silicone-hydrogel lens.

3. The method of claim 2, wherein the chloroauric acid has a concentration of about 0.1-5% and wherein the citric acid has a concentration of 2-15 times the concentration of the chloroauric acid.

4. The method of claim 3, wherein the ratio of citric acid to chloroauric acid is from about 1 to 15.

5. The method of claim 1, wherein the gold chloride solution has a concentration of 1% and the mixture of citric acid and gold chloride has a gold chloride concentration of 1% and a citric acid concentration of 10%.

6. The method of claim 1, wherein reduction of gold chloride to form the gold particles is achieved by reducing molecules loaded into the contact lens or integrated into the contact lens matrix.

7. The method of claim 6, wherein the reducing molecules comprise citric acid or a water-soluble salt thereof, oxalic acid or a water-soluble salt thereof, salicylic acid or a water-soluble salt thereof, glucose, hydroquinone, bromohydroquinone, chlorohydroquinone, methyl-hydroquinone, dimethyl-hydroquinone;

sodium sulfite, potassium sulfite, or a mixture thereof.

8. The method of claim 1, wherein the gold nanoparticles have a concentration of about 1-5%.

9. The method of claim 1, wherein the gold nanoparticles have an average particle size of about 10-40 nm.

10. The method of claim 1, wherein the gold nanoparticles have an average diameter of about 200 nm.

11. A contact lens formed by the method of claim 1.

* * * * *